US012599765B2

(12) United States Patent
Halavee et al.

(10) Patent No.: US 12,599,765 B2
(45) Date of Patent: *Apr. 14, 2026

(54) SHIFTING OF TRANSDUCER ARRAY TO REDUCE SKIN IRRITATION

(71) Applicant: Novocure GmbH, Root (CH)

(72) Inventors: Noa Halavee, Tel Aviv (IL); Boaz Marsault, Haifa (IL); Elie Yaacobi, Haifa (IL); Golan Bar-Tal, Haifa (IL); Nitzan Shany, Haifa (IL)

(73) Assignee: Novocure GmbH, Baar (CH)

( * ) Notice: Subject to any disclaimer, the term of this patent is extended or adjusted under 35 U.S.C. 154(b) by 535 days.

This patent is subject to a terminal disclaimer.

(21) Appl. No.: 18/080,091

(22) Filed: Dec. 13, 2022

(65) Prior Publication Data

US 2023/0181899 A1      Jun. 15, 2023

Related U.S. Application Data

(60) Provisional application No. 63/324,491, filed on Mar. 28, 2022, provisional application No. 63/289,484, filed on Dec. 14, 2021.

(51) Int. Cl.
| | |
|---|---|
| *A61N 1/36* | (2006.01) |
| *A61N 1/04* | (2006.01) |
| *A61N 1/40* | (2006.01) |

(52) U.S. Cl.
CPC ....... *A61N 1/36002* (2017.08); *A61N 1/0476* (2013.01)

(58) Field of Classification Search
CPC ..... A61N 1/36002; A61N 1/0476; A61N 1/06
See application file for complete search history.

(56) References Cited

U.S. PATENT DOCUMENTS

| | | | |
|---|---|---|---|
| 6,327,487 | B1 | 12/2001 | Stratbucker |
| 6,376,393 | B1 | 4/2002 | Newton et al. |

(Continued)

FOREIGN PATENT DOCUMENTS

| | | |
|---|---|---|
| CN | 112930209 A | 6/2021 |
| CN | 113577535 A | 11/2021 |

(Continued)

OTHER PUBLICATIONS

International Search Report and Written Opinion issued in International Application No. PCT/IB2022/062152 mailed Feb. 20, 2023.

(Continued)

*Primary Examiner* — Joseph A Stoklosa
*Assistant Examiner* — Annie L Shoulders
(74) *Attorney, Agent, or Firm* — McCarter & English, LLP; Michael A. Sartori

(57) ABSTRACT

A transducer apparatus for delivering tumor treating fields to a subject's body, the transducer apparatus including: an array of electrodes, the array configured to be positioned over the subject's body with a face of the array facing the subject's body, the array including electrode elements positioned in existing electrode positions arranged around a centroid of the array; and at least one void space in the array capable of enclosing an areal footprint equivalent to at least 40% of an areal footprint of at least one existing electrode position, and superimposable on at least 40% of at least one existing electrode position by rotation of the array around the centroid.

20 Claims, 8 Drawing Sheets

(56) References Cited

U.S. PATENT DOCUMENTS

| | | | |
|---|---|---|---|
| 6,868,289 B2 | 3/2005 | Palti | |
| 7,016,725 B2 | 3/2006 | Palti | |
| 7,089,054 B2 | 8/2006 | Palti | |
| 7,136,699 B2 | 11/2006 | Palti | |
| 7,333,852 B2 | 2/2008 | Palti | |
| 7,467,011 B2 | 12/2008 | Palti | |
| 7,519,420 B2 | 4/2009 | Palti | |
| 7,565,205 B2 | 7/2009 | Palti | |
| 7,565,206 B2 | 7/2009 | Palti | |
| 7,599,745 B2 | 10/2009 | Palti | |
| 7,599,746 B2 | 10/2009 | Palti | |
| 7,706,890 B2 | 4/2010 | Palti | |
| 7,715,921 B2 | 5/2010 | Palti | |
| 7,805,201 B2 | 9/2010 | Palti | |
| 7,890,183 B2 | 2/2011 | Palti et al. | |
| 7,912,540 B2 | 3/2011 | Palti | |
| 7,917,227 B2 | 3/2011 | Palti | |
| 8,019,414 B2 | 9/2011 | Palti | |
| 8,027,738 B2 | 9/2011 | Palti | |
| 8,170,684 B2 | 5/2012 | Palti | |
| 8,175,698 B2 | 5/2012 | Palti et al. | |
| 8,229,555 B2 | 7/2012 | Palti | |
| RE43,618 E | 8/2012 | Palti | |
| 8,244,345 B2 | 8/2012 | Palti | |
| 8,406,870 B2 | 3/2013 | Palti | |
| 8,447,395 B2 | 5/2013 | Palti et al. | |
| 8,447,396 B2 | 5/2013 | Palti et al. | |
| 8,465,533 B2 | 6/2013 | Palti | |
| 8,706,261 B2 | 4/2014 | Palti | |
| 8,718,756 B2 | 5/2014 | Palti | |
| 8,764,675 B2 | 7/2014 | Palti | |
| 9,023,090 B2 | 5/2015 | Palti | |
| 9,023,091 B2 | 5/2015 | Palti | |
| 9,039,674 B2 | 5/2015 | Palti et al. | |
| 9,056,203 B2 | 6/2015 | Palti et al. | |
| 9,440,068 B2 | 9/2016 | Palti et al. | |
| 9,655,669 B2 | 5/2017 | Palti et al. | |
| 9,750,934 B2 | 9/2017 | Palti et al. | |
| 9,910,453 B2 | 3/2018 | Wasserman et al. | |
| 10,188,851 B2 | 1/2019 | Wenger et al. | |
| 10,441,776 B2 | 10/2019 | Kirson et al. | |
| 10,779,875 B2 | 9/2020 | Palti et al. | |
| 10,967,167 B2 | 4/2021 | Hagemann et al. | |
| 11,103,698 B2 | 8/2021 | Chang et al. | |
| 11,191,956 B2 | 12/2021 | Giladi et al. | |
| 12,268,863 B2 * | 4/2025 | Halavee | A61N 1/403 |
| 2004/0176804 A1 | 9/2004 | Palti | |
| 2005/0015134 A1 | 1/2005 | Carim | |
| 2006/0167499 A1 | 7/2006 | Palti | |
| 2006/0276858 A1 | 12/2006 | Palti | |
| 2007/0225766 A1 | 9/2007 | Palti | |
| 2007/0239213 A1 | 10/2007 | Palti | |
| 2009/0076366 A1 | 3/2009 | Palti | |
| 2010/0185078 A1 | 7/2010 | Wilfinger et al. | |
| 2012/0029419 A1 | 2/2012 | Palti | |
| 2012/0283726 A1 | 11/2012 | Palti | |
| 2013/0066412 A1 | 3/2013 | Van Der Beek et al. | |
| 2014/0330268 A1 | 11/2014 | Palti et al. | |
| 2017/0112983 A1 | 4/2017 | Thorne et al. | |
| 2017/0120041 A1 | 5/2017 | Wenger et al. | |
| 2017/0215939 A1 | 8/2017 | Palti et al. | |
| 2017/0281934 A1 | 10/2017 | Giladi et al. | |
| 2018/0001075 A1 | 1/2018 | Kirson et al. | |
| 2018/0001078 A1 | 1/2018 | Kirson et al. | |
| 2018/0008708 A1 | 1/2018 | Giladi et al. | |
| 2018/0050200 A1 | 2/2018 | Wasserman et al. | |
| 2018/0160933 A1 | 6/2018 | Urman et al. | |
| 2018/0202991 A1 | 7/2018 | Giladi et al. | |
| 2018/0280687 A1 | 10/2018 | Carter et al. | |
| 2019/0086741 A1 | 3/2019 | Milton | |
| 2019/0117956 A1 | 4/2019 | Wenger et al. | |
| 2019/0117963 A1 | 4/2019 | Travers et al. | |
| 2019/0224474 A1 | 7/2019 | Yang et al. | |
| 2019/0308016 A1 | 10/2019 | Wenger et al. | |
| 2020/0001069 A1 | 1/2020 | Kirson et al. | |
| 2020/0009376 A1 | 1/2020 | Chang et al. | |
| 2020/0009377 A1 | 1/2020 | Chang et al. | |
| 2020/0016067 A1 | 1/2020 | Gotlib et al. | |
| 2020/0023179 A1 | 1/2020 | Bomzon et al. | |
| 2020/0061360 A1 | 2/2020 | Hagemann et al. | |
| 2020/0061361 A1 | 2/2020 | Hagemann et al. | |
| 2020/0069937 A1 | 3/2020 | Naveh et al. | |
| 2020/0078582 A1 | 3/2020 | Alon et al. | |
| 2020/0108031 A1 | 4/2020 | Borst et al. | |
| 2020/0114141 A1 | 4/2020 | Bomzon et al. | |
| 2020/0114142 A1 | 4/2020 | Bomzon et al. | |
| 2020/0121728 A1 | 4/2020 | Wardak et al. | |
| 2020/0129761 A1 | 4/2020 | Bomzon et al. | |
| 2020/0146586 A1 | 5/2020 | Naveh et al. | |
| 2020/0155835 A1 | 5/2020 | Wasserman et al. | |
| 2020/0171297 A1 | 6/2020 | Kirson et al. | |
| 2020/0179512 A1 | 6/2020 | Giladi et al. | |
| 2020/0219261 A1 | 7/2020 | Shamir et al. | |
| 2020/0269037 A1 | 8/2020 | Hagemann et al. | |
| 2020/0269041 A1 | 8/2020 | Zeevi et al. | |
| 2020/0269042 A1 | 8/2020 | Giladi et al. | |
| 2020/0269043 A1 | 8/2020 | Wasserman et al. | |
| 2020/0368525 A1 | 11/2020 | Maag et al. | |
| 2021/0031031 A1 | 2/2021 | Wasserman et al. | |
| 2021/0038584 A1 | 2/2021 | Voloshin-Sela | |
| 2021/0060334 A1 | 3/2021 | Avraham et al. | |
| 2021/0069503 A1 | 3/2021 | Tran et al. | |
| 2021/0138233 A1 | 5/2021 | Deslauriers | |
| 2021/0162228 A1 | 6/2021 | Urman et al. | |
| 2021/0177492 A1 | 6/2021 | Travers et al. | |
| 2021/0185975 A1 | 6/2021 | Strauss et al. | |
| 2021/0187277 A1 | 6/2021 | Wasserman et al. | |
| 2021/0196348 A1 | 7/2021 | Wasserman | |
| 2021/0199640 A1 | 7/2021 | Patel et al. | |
| 2021/0203250 A1 | 7/2021 | Wasserman | |
| 2021/0268247 A1 | 9/2021 | Story et al. | |
| 2021/0299440 A1 | 9/2021 | Deslauriers et al. | |
| 2021/0308446 A1 | 10/2021 | Alon et al. | |
| 2021/0330950 A1 | 10/2021 | Hagemann et al. | |
| 2021/0346694 A1 | 11/2021 | Wasserman et al. | |
| 2021/0379362 A1 | 12/2021 | Smith et al. | |
| 2021/0408383 A1 | 12/2021 | Kalra et al. | |
| 2022/0095997 A1 | 3/2022 | Wasserman | |
| 2022/0096821 A1 | 3/2022 | Kirson et al. | |
| 2022/0096854 A1 | 3/2022 | Carlson | |
| 2022/0118249 A1 | 4/2022 | Bomzon et al. | |
| 2022/0161028 A1 | 5/2022 | Giladi et al. | |
| 2022/0193435 A1 | 6/2022 | Wasserman et al. | |
| 2022/0267445 A1 | 8/2022 | Tran et al. | |
| 2022/0280787 A1 | 9/2022 | Bomzon et al. | |
| 2022/0288395 A1 | 9/2022 | Voloshin-Sela et al. | |
| 2022/0305276 A1 | 9/2022 | Marciano et al. | |
| 2022/0313992 A1 | 10/2022 | Wasserman | |
| 2022/0323753 A1 | 10/2022 | Voloshin-Sela et al. | |
| 2022/0387784 A1 | 12/2022 | Kirson et al. | |
| 2022/0395699 A1 | 12/2022 | Doyle | |
| 2022/0409893 A1 | 12/2022 | Wasserman et al. | |
| 2023/0000384 A1 | 1/2023 | Wasserman et al. | |
| 2023/0001197 A1 | 1/2023 | Wasserman et al. | |
| 2023/0001221 A1 | 1/2023 | Farber | |
| 2023/0009366 A1 | 1/2023 | Voloshin-Sela et al. | |
| 2023/0019638 A1 | 1/2023 | Wasserman | |
| 2023/0037806 A1 | 2/2023 | Wasserman et al. | |
| 2023/0043071 A1 | 2/2023 | Wasserman et al. | |
| 2023/0065587 A1 | 3/2023 | Shnaiderman et al. | |
| 2023/0098801 A1 | 3/2023 | Carlson | |
| 2023/0141087 A1 | 5/2023 | Giladi et al. | |
| 2023/0149704 A1 | 5/2023 | Wasserman et al. | |
| 2023/0181919 A1 | 6/2023 | Wendel et al. | |
| 2023/0188055 A1 | 6/2023 | Wasserman | |
| 2023/0302289 A1 | 9/2023 | Halavee et al. | |
| 2024/0009475 A1 * | 1/2024 | Halavee | A61N 1/40 |
| 2024/0042203 A1 * | 2/2024 | Gill | A61N 1/36034 |

FOREIGN PATENT DOCUMENTS

| | | | |
|---|---|---|---|
| CN | 215691050 U | 2/2022 | |
| JP | 2002-502517 A | 1/2002 | |
| JP | 2017-522099 A | 8/2017 | |

(56) References Cited

FOREIGN PATENT DOCUMENTS

| KR | 20070010908 | A | 1/2007 |
|---|---|---|---|
| WO | WO-2014/110071 | A2 | 7/2014 |
| WO | WO-2021/226353 | A1 | 11/2021 |
| WO | WO-2021224678 | A1 | 11/2021 |
| WO | 2022/200964 | A1 | 9/2022 |
| WO | WO-2023017492 | A2 | 2/2023 |
| WO | WO-2023/100103 | A1 | 6/2023 |
| WO | WO-2024/165920 | A1 | 8/2024 |
| WO | WO-2024/165995 | A1 | 8/2024 |

OTHER PUBLICATIONS

Cornelia Wenger et al., "A Review on Tumor-Treating Fields (TTFields): Clinical Implications Inferred from Computational Modeling," IEEE Reviews in Biomedical Engineering, vol. 11, Feb. 13, 2018, pp. 195-207.
Unknown, "Omni-Wave by Flexcon," Flexcon Healthcare, www.FLEXcon.com/OMNI-WAVE, 2023.
Unknown, "Skin Contact Applications—Electrodes & Wearables," FLEXcon, www.FLEXcon.com, 2023.
International Search Report issued in application No. PCT/IB2022/058124 dated Nov. 20, 2022.

* cited by examiner

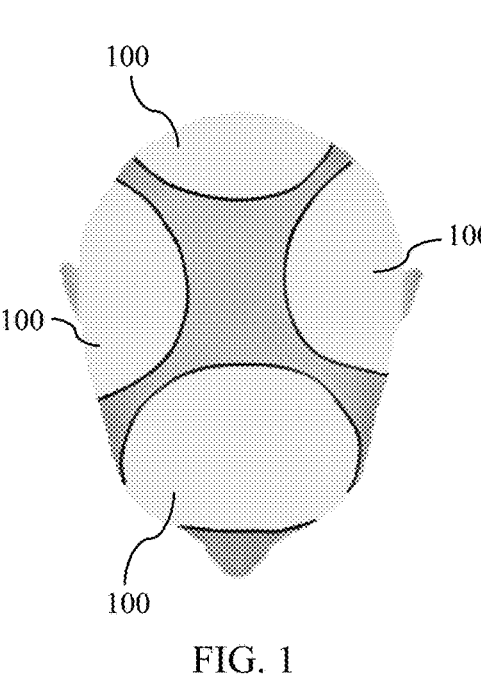
FIG. 1
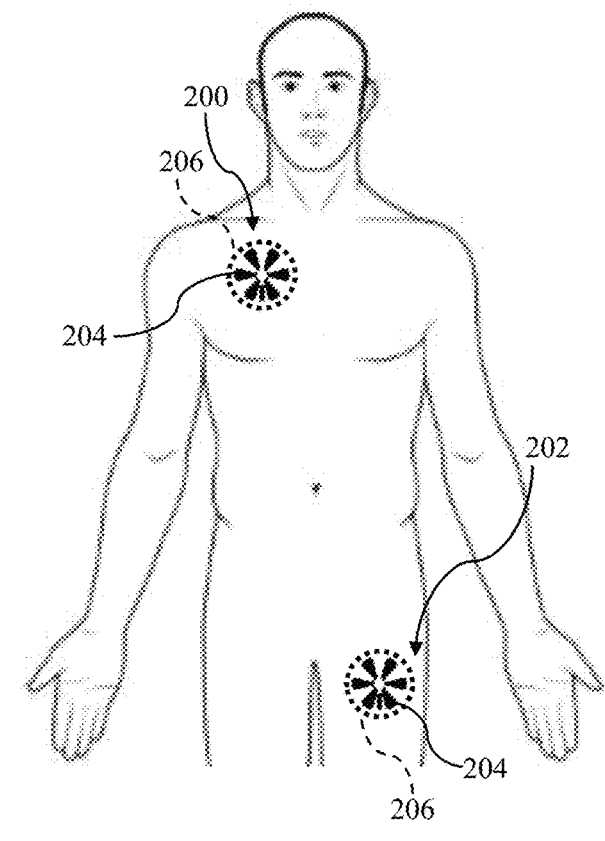
FIG. 2
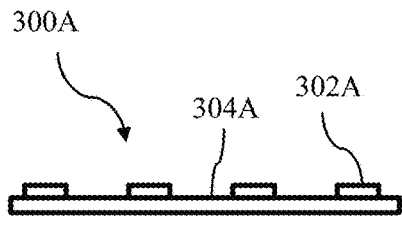
FIG. 3A
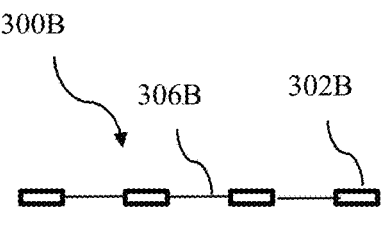
FIG. 3B
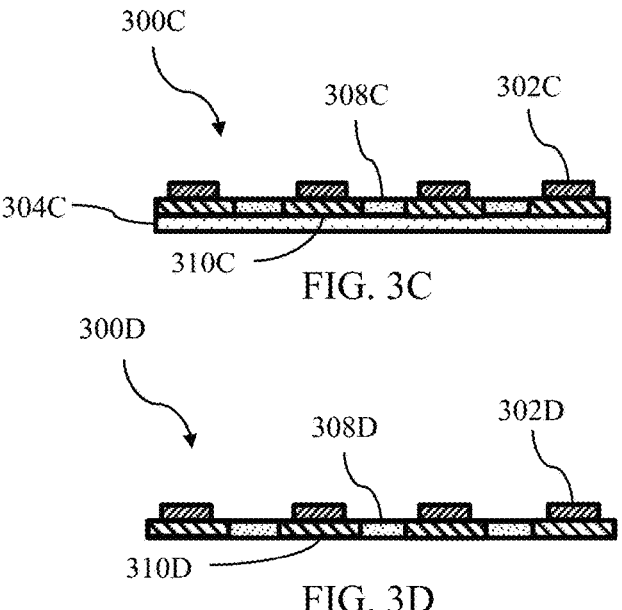
FIG. 3C
FIG. 3D

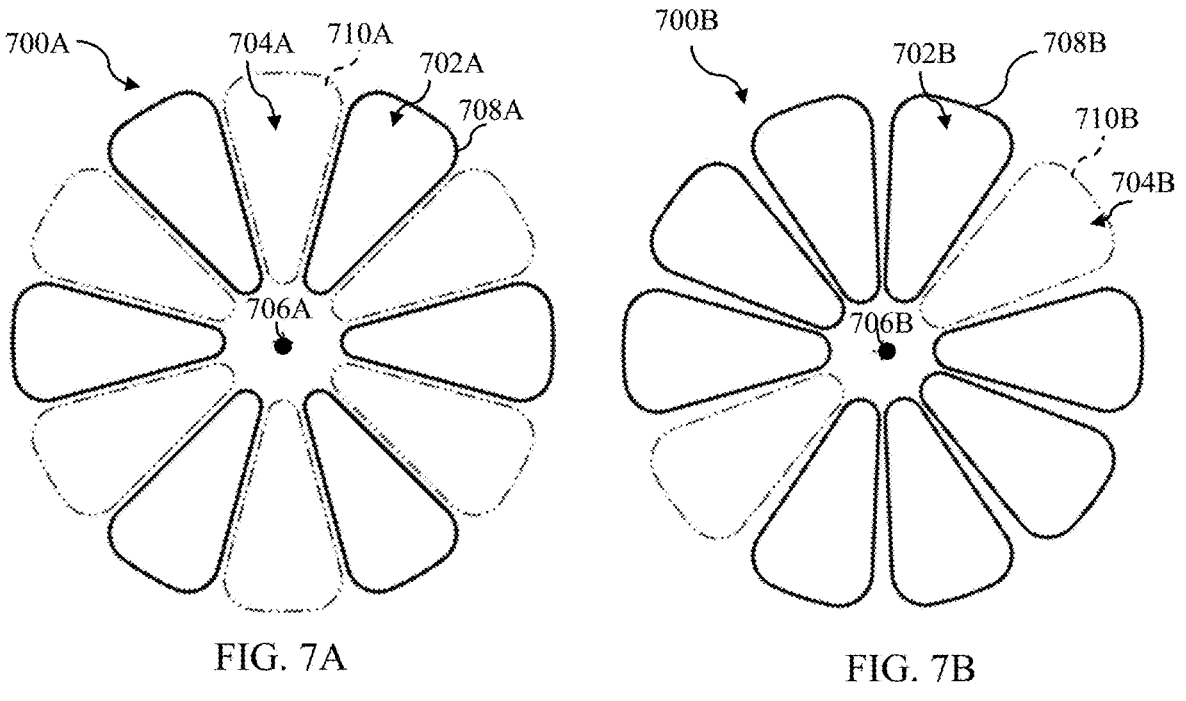
FIG. 7A                  FIG. 7B
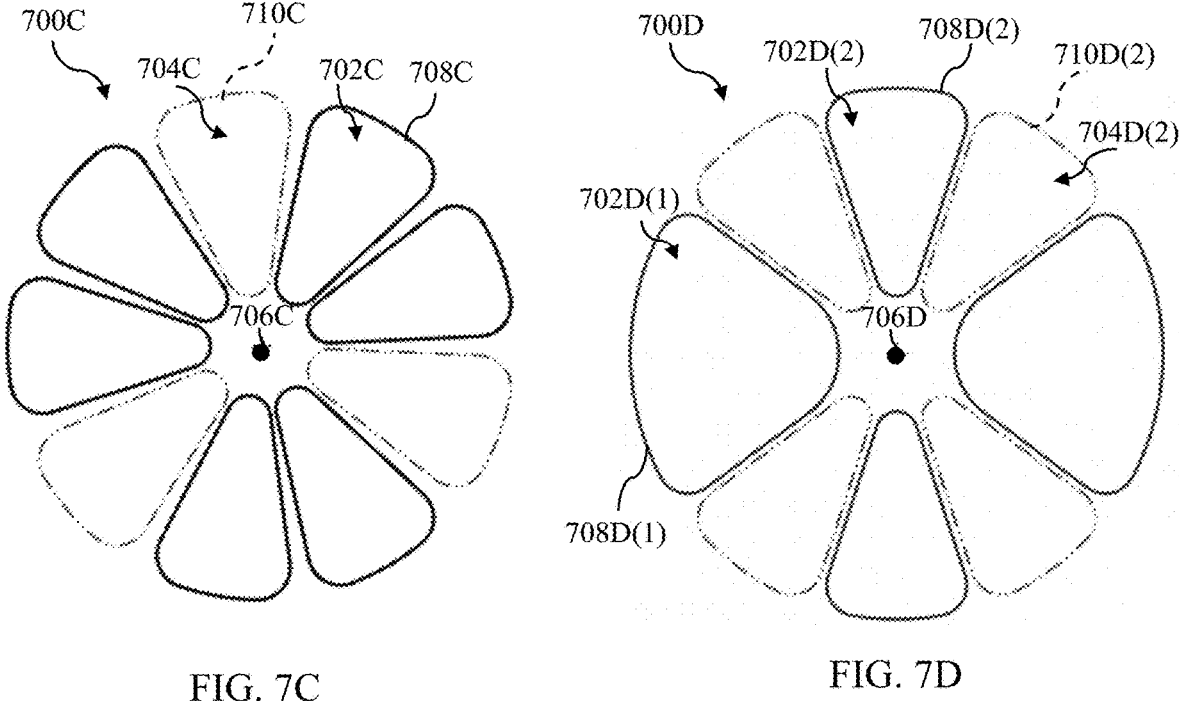
FIG. 7C                  FIG. 7D

SHIFTING OF TRANSDUCER ARRAY TO REDUCE SKIN IRRITATION

CROSS REFERENCE TO RELATED APPLICATIONS

This application claims priority to U.S. Provisional Patent Application No. 63/289,484, filed Dec. 14, 2021 and U.S. Provisional Patent Application No. 63/324,491, filed Mar. 28, 2022, both of which are hereby incorporated by reference in their entirety.

BACKGROUND

Tumor treating fields (TTFields) are low intensity alternating electric fields within the intermediate frequency range (for example, 50 kHz to 1 MHz), which may be used to treat tumors as described in U.S. Pat. No. 7,565,205. TTFields are induced non-invasively into the region of interest by transducers placed on the patient's body and applying AC voltages between the transducers. Conventionally, transducers used to generate TTFields include a plurality of electrode elements comprising ceramic disks. One side of each ceramic disk is positioned against the patient's skin, and the other side of each disc has a conductive backing. Electrical signals are applied to this conductive backing, and these signals are capacitively coupled into the patient's body through the ceramic discs. Conventional transducer designs include rectangular arrays of ceramic disks aligned with each other in straight rows and columns and attached to the subject's body via adhesive.

BRIEF DESCRIPTION OF THE DRAWINGS

FIG. 1 depicts an example of transducers located on a subject's head.

FIG. 2 depicts an example of transducers located on a subject's body.

FIGS. 3A-3D are cross-sectional views of example structures of transducers.

FIGS. 7A-7I depict example layouts of arrays of electrode elements and relief regions.

FIG. 8 depicts another example layout of an array of electrode elements and relief regions.

DESCRIPTION OF EMBODIMENTS

Figure 4A:
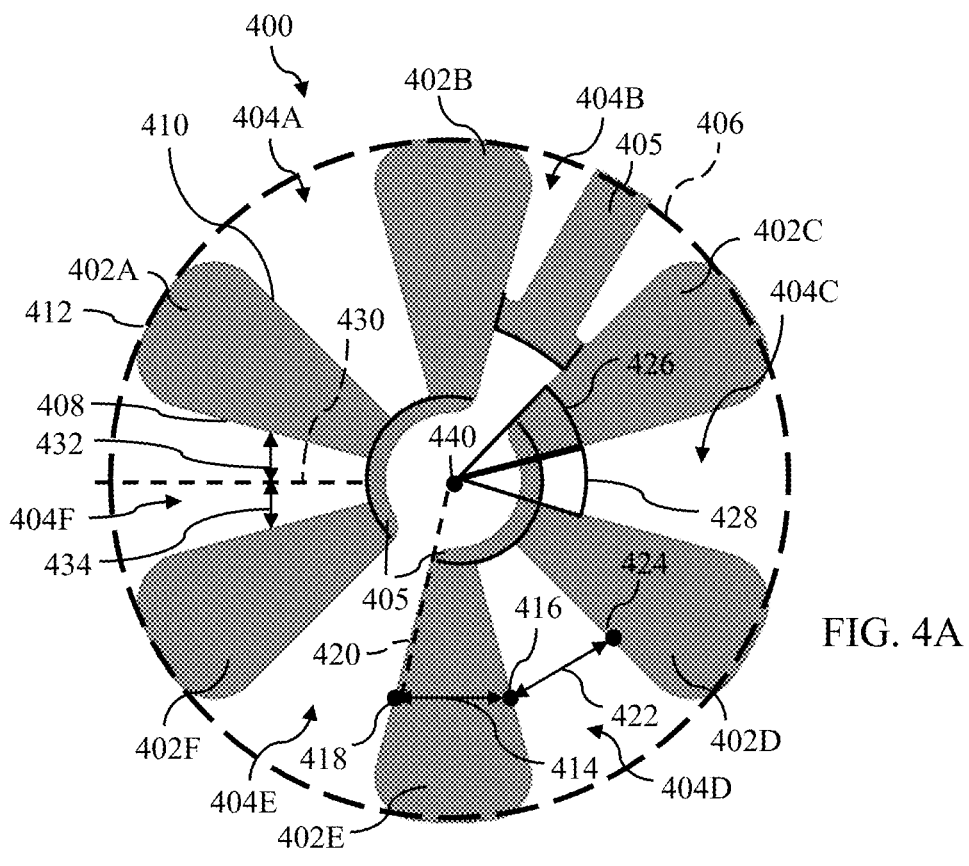
FIGS. 4A and 4B depict an example layout of an array of electrode elements on a transducer apparatus (FIG. 4A) and the array after rotation about its centroid (FIG. 4B).

This application describes exemplary transducer apparatuses used to apply TTFields to a subject's body for treating one or more cancers. This application also describes exemplary methods to apply TTFields to a subject's body using transducers.

Transducers used to apply TTFields to a subject's body often include multiple electrode elements electrically coupled together on a substrate and attached to the subject's body at a desired location, for example, via an adhesive backing of the substrate or a separately applied adhesive. Conventional transducers have large, rectangular surfaces so as to maximize a number of electrode elements that are located on the transducer for applying TTFields to the subject's body. However, subjects can experience skin irritation on portions of their skin that are contacted by the electrode elements during TTField treatment.

The inventors have now recognized that a need exists for transducers that can be shifted to reduce, minimize, prevent, soothe, heal, or treat skin irritation without significantly changing the field intensity of TTFields being induced in the subject's body. For example, transducers that are able to be shifted so that skin previously contacted by electrode elements can be uncovered (or covered by a topical medication) without substantially moving the transducer from an optimal location on the subject's body are desired. The new position of the transducer after shifting is in substantially the same location if the footprint of the new position after shifting covers greater than or equal to 80% of the footprint of the original position before shifting; or if it covers greater than or equal to 90% of the footprint of the original position before shifting; or if it covers greater than or equal to 95% of the footprint of the original position before shifting. In some embodiments, the footprint of the new position of the transducer after shifting covers 100% of the footprint of the original position of the transducer before shifting. The shifting of the transducer apparatuses can reduce, minimize, prevent, soothe, heal, and/or treat skin irritation while maintaining the transducer in an optimal location on the subject's body. As a result, the transducers can continuously induce TTFields at an ideal location and power level for targeting a region of interest (e.g., tumor) in the subject's body, thereby improving patient outcomes.

The disclosed transducer apparatuses can be shifted via rotation about a centroid of the array of electrodes, or via translation of the array of electrodes, so that one or more portions of the subject's skin that were previously contacted by electrode elements can be uncovered (or covered by a medication), while maintaining an optimal location of the transducer on the subject's body. In some embodiments, the array of electrodes does not comprise an electrode position that encompasses the centroid of the array. The disclosed transducer apparatuses may have a substantially rounded shape enabling the transducers to be positioned on a subject's head. In other examples, the disclosed transducer apparatus may have other (e.g., non-rounded) shapes. Descriptions of embodiments related to specific exemplary Figures herein may be applicable, and may be combined with, descriptions of embodiments related to other exemplary Figures herein unless otherwise indicated herein or otherwise clearly contradicted by context.

FIG. 1 depicts transducers 100 positioned on the head of a subject's body. Such arrangement of transducers 100 is capable of applying TTFields to a tumor in a region of the subject's brain. Various other positions and/or orientations on the subject's head may be selected for placement of transducers. Each transducer 100 may have an array of electrode elements disposed thereon. Each transducer 100 may be placed on a subject's head with a face of the array of electrode elements facing and conforming to the subject's head. As illustrated, the transducers 100 on the subject's head do not overlap one another, e.g., due to their rounded shape.

FIG. 2 depicts transducers 200 and 202 attached to other portions (e.g., a thorax/torso and a thigh) of the subject's body. The transducers 200 and 202 may be affixed to the subject's body via a medically appropriate gel or adhesive. In other embodiments, the transducers 200 and 202 may be attached to one or more garments and held against the subject's body. Each of the transducers 200 and 202 may have an array of electrode elements 204 disposed thereon. Each transducer 200 and 202 may be placed over the subject's body with a face of the array of electrode elements facing and conforming to the subject's body.

Figures 7E, 7F, 7G:
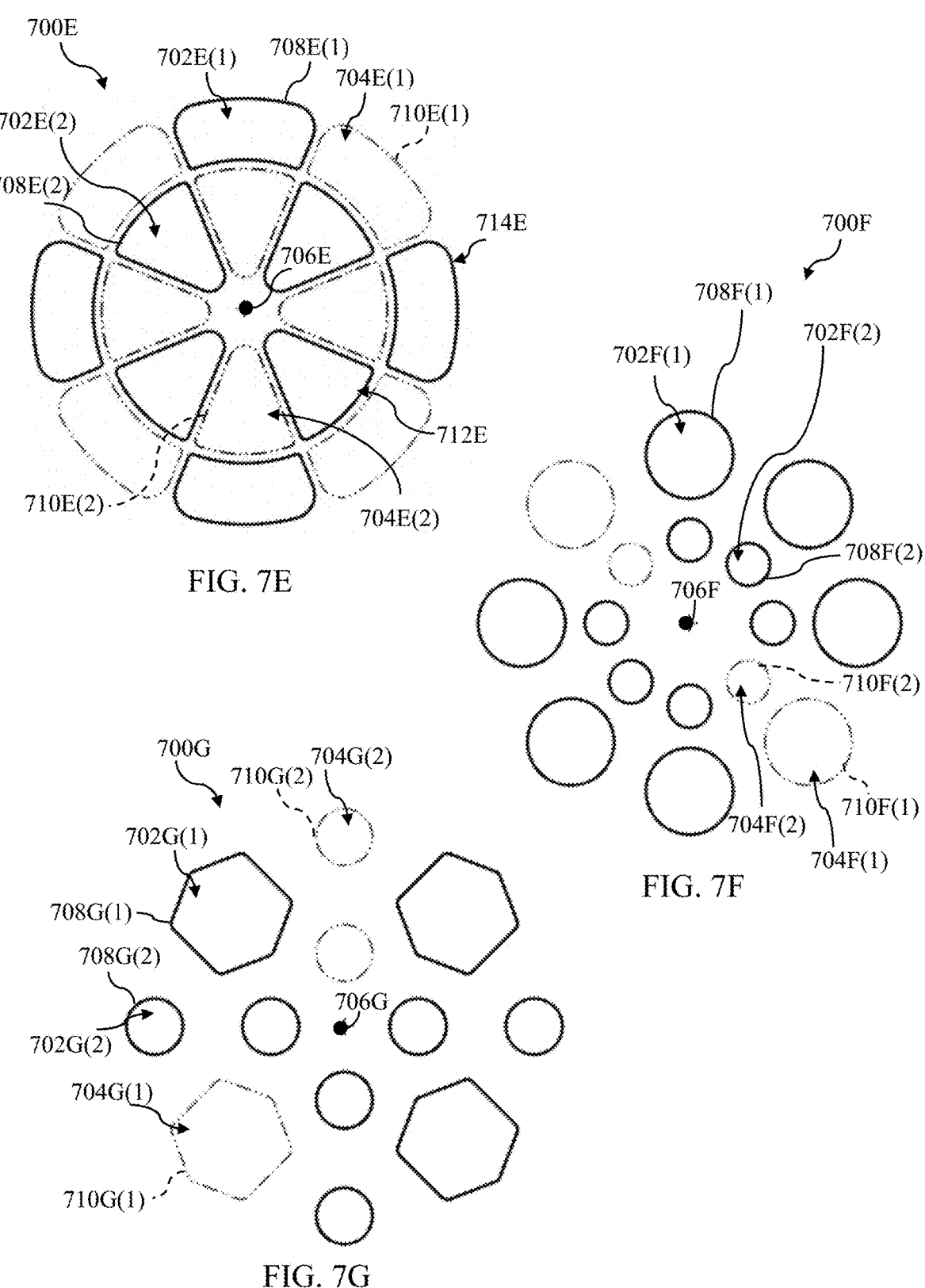
Figures 7H, 7I, 8:
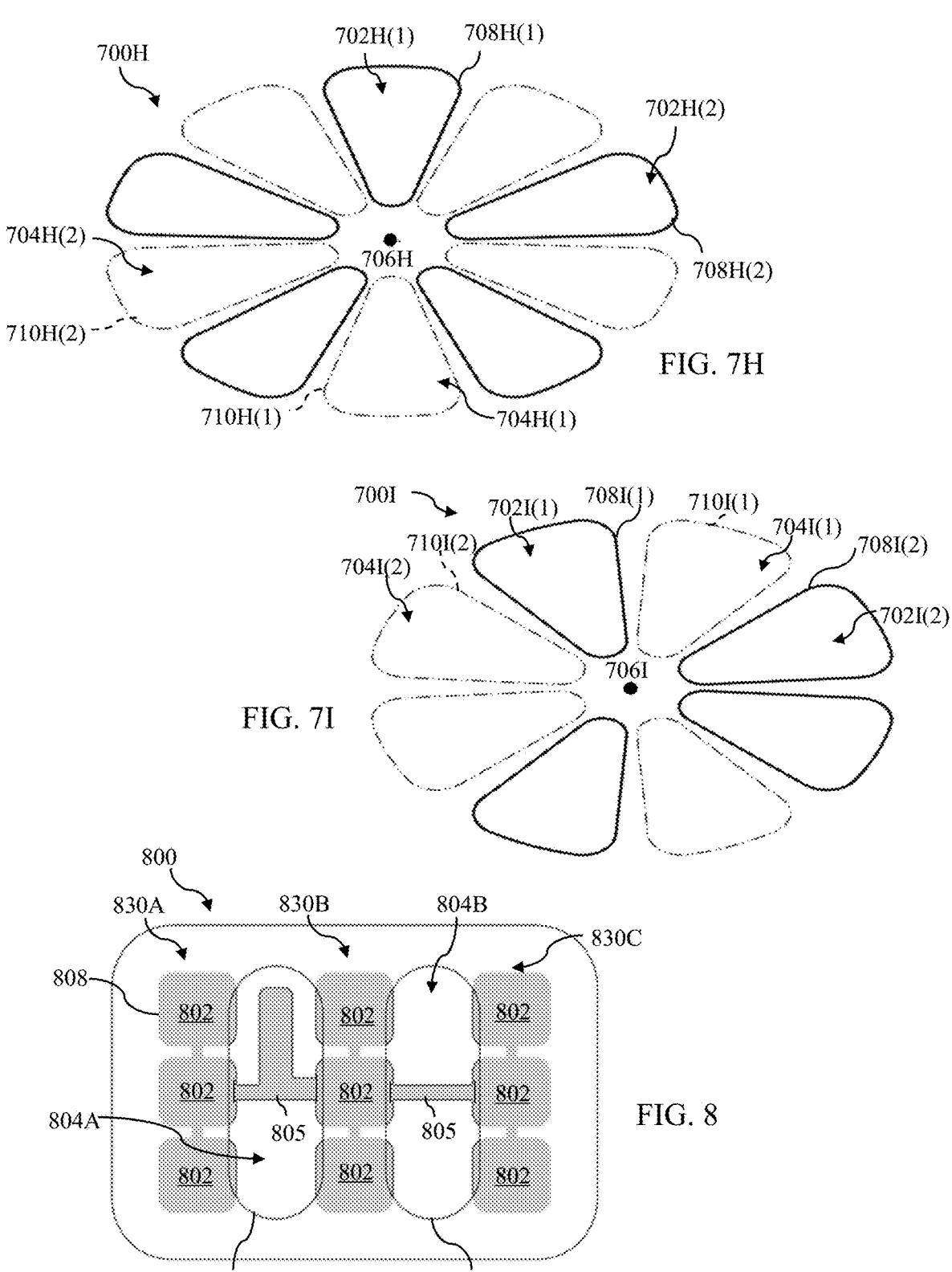

In the first transducer 200 and the second transducer 202, an outer perimeter 206 (defined by a dashed line in FIG. 2) traces the array of electrode elements 204. In an example, the outer perimeter 206 of the array on each transducer may have a substantially rounded edge. The outer perimeter 206 may be substantially circular, oval, ovaloid, ovoid, or elliptical in shape. For example, as illustrated, the outer perimeter 206 may have a circular shape. In another example, the outer perimeter 206 may have other shapes such as, for example, a square or rectangular shape or substantially square or rectangular shape with rounded corners (e.g., as shown in FIG. 8).

The structure of the transducers may take many forms. In FIG. 3A, the transducer 300A has a plurality of electrode elements 302A positioned on a substrate 304A. The substrate 304A is configured for attaching the transducer 300A to a subject's body. Suitable materials for the substrate 304A include, for example, cloth, foam, flexible plastic, and/or a conductive medical gel. The transducer 300A may be affixed to the subject's body via the substrate 304A (e.g., via an adhesive layer and/or a conductive medical gel). The adhesive layer that contacts the subject's skin may be present around the outer perimeter of the array of electrodes, and/or may be present between one or more gaps between electrodes. Alternatively, areas between electrodes may be non-adhesive regions. The transducer may be conductive or non-conductive. FIG. 3B depicts another example of the structure of the transducer 300B. In this example, the transducer 300B includes a plurality of electrode elements 302B that are electrically and mechanically connected to one another without a substrate. In one example, electrode elements 302B are connected to each other through conductive wires 306B.

In FIGS. 3C and 3D, the transducers 300C and 300D include one or more medication regions 308C and 308D, respectively. The medication regions 308C and 308D may be non-adhesive regions. For example, no exposed adhesive is present in the medication region(s) 308C and 308D. The medication region(s) 308C and 308D may each comprise a medication substrate. The medication substrate may be capable of at least one of receiving, absorbing, or holding a topical medication applied thereto. The medication substrate may comprise a cloth, a gauze, a non-woven material, a foam, or a sponge located between one or more pairs of electrode elements 302C and 302D. In an example, the medication region(s) 308C and 308D may also comprise a topical medication integrated in or on the medication substrate. The topical medication may comprise a base component of oil, water, petrolatum, wax, cellulose, or a combination thereof. The topical medication may be a cream, an ointment, a lotion, a gel, a wax, a paste, or a mineral oil jelly. The topical medication may comprise at least one of an antibiotic, a steroid, an antiseptic, an emollient, an anesthetic, a terpene, a plant extract, a silicon-based organic polymer, an antifungal agent, a burn relief agent, a skin repair agent, an astringent, or an antihistamine. The topical medication may be any desired compound capable of soothing, healing, and/or providing relief for inflammation, sores, or other irritation that may develop on the skin of the subject's body. The topical medication may be substantially evenly distributed through a thickness of the medication substrate to form the medication regions 308C and 308D. Alternatively, the topical medication may be substantially disposed on the surface of the medication substrate to form the medication regions 308C and 308D.

As shown in FIG. 3C, the transducer 300C may include a transducer substrate 304C that is separate from the medication region(s) 308C. The array of electrode elements 302C may be disposed on a surface of the transducer substrate 304C, and the transducer substrate 304C may include an adhesive layer 310C for attaching the transducer apparatus to the subject's body. The medication substrate may be a portion of the transducer substrate 304C, or may be disposed on the surface of the transducer substrate 304C. Thus, the medication region 308C may be disposed on the surface of the transducer substrate 304C (as shown in FIG. 3C). In other embodiments, for example as shown in FIG. 3D, the transducer 300D may not include a transducer substrate, but rather merely an adhesive layer 310D for attaching the transducer 300D to the subject's body, and the medication region(s) 308D may be coupled between different portions of the adhesive layer 310D and span a distance between electrode elements 302D.

The transducers 300A, 300B, 300C, and 300D may comprise arrays of substantially flat electrode elements 302A, 302B, 302C, and 302D, respectively. The array of electrode elements may be capacitively coupled. The electrode elements 302A, 302B, 302C, and 302D may be non-ceramic dielectric materials positioned over a plurality of flat conductors such as, for example, polymer films disposed over pads on a printed circuit board or over flat pieces of metal. In another example, the electrode elements 302A, 302B, 302C, and 302D are ceramic elements.

FIGS. 4A-7I illustrate examples of transducer apparatuses that may be used to apply TTFields to a subject's body. Each example transducer apparatus enables a simple rotation of the transducer to reposition at least one non-adhesive void region formed in the electrode array (or, alternatively, at least one medication region as described above with reference to FIGS. 3C and 3D) over an area of the subject's skin that was previously covered by an electrode element. Positioning a void region over the area of the subject's skin that was previously covered by an electrode element allows this area of the subject's skin to "breathe" and recover from the prior contact it had with the electrode element used to induce TTFields.

As some subjects experience skin irritation in response to prolonged interaction of the skin with the electrode elements used to induce TTFields, moving the transducer so that a void is positioned over an affected area of the subject's skin may help to minimize, reduce, or prevent irritation of the subject's skin throughout TTField treatment. In addition, positioning a medication region over the area of the subject's skin that was previously covered by an electrode element allows an application of a topical medication to this area of the subject's skin to soothe, heal, reduce inflammation or soreness, or otherwise improve the condition of the subject's skin. Since the transducer apparatus may be rotated about a centroid of the array of electrodes, this allows the transducer to continue outputting TTFields from the same optimal location on the subject's body during treatment while providing relief and/or healing to areas of the subject's skin.

Figure 4B:
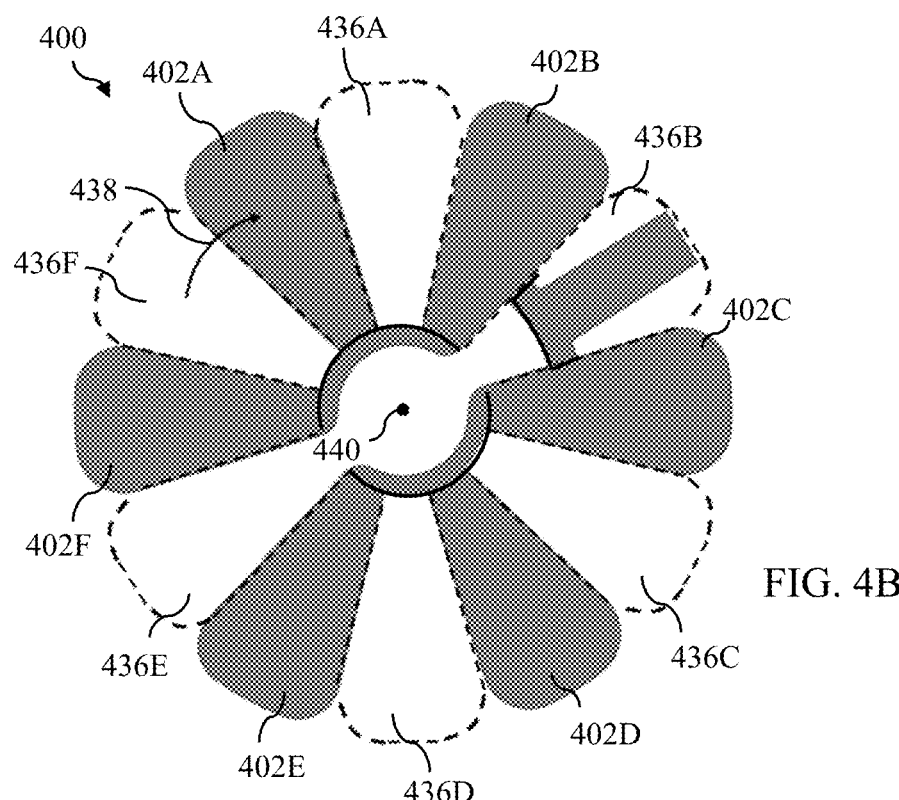

FIGS. 4A and 4B depict an example transducer apparatus 400, which may include an array of electrodes 402 (i.e., 402A-F) configured to be positioned over the subject's body with a face of the array facing the subject's body. FIGS. 4A and 4B illustrate the transducer apparatus 400 as viewed from a direction perpendicular to this face of the array. As shown in FIG. 4A, the transducer apparatus 400 may also include one or more blank spaces 404 (i.e., 404A-F), which do not overlap with any electrodes 402. At least part of one or more of the blank spaces 404 may be a relief region, defined herein as either 1) void regions of the transducer apparatus 400 that are fully uncovered other than the transducer substrate, or 2) non-adhesive regions comprising a medication substrate capable of receiving, absorbing, or holding a topical medication applied thereto, or 3) medication regions of the transducer apparatus comprising a medication substrate and a topical medication integrated therein or thereon used to administer a topical medication to an area of the subject's skin. The topical medication may cover the entire surface of the medication substrate or may cover some portion of it; or it may be infused through some or the entire thickness of the medication substrate below the entire areal surface of the medication substrate or below an areal portion thereof; or it may be located in some combination of these. The areal footprint of the medication substrate may fill the entire area of the blank space or some portion thereof. In some embodiments, the medication region has a surface area sufficient enough to occupy at least 40%, or at least 50%, of one of the electrodes of the array of electrodes. In some embodiments, the medication region has a surface area sufficient enough to occupy at least 95%, or at least 100%, of one of the electrodes of the array of electrodes. In some embodiments, the medication substrate is a portion of the transducer substrate. The array of electrodes 402 may be spaced about a centroid 440 of the array, and the blank spaces 404 may each be located between two adjacent electrodes. In some embodiments, the transducer apparatus 400 has an alternating pattern of electrodes 402 and blank spaces 404. In other embodiments, non-alternating rotational patterns of electrodes 402 and blank spaces 404 may be used. The electrodes 402 may be electrically coupled together via one or more PCB layer(s)/connector(s) 405 or wire(s). The PCB layer(s)/connector(s) 405 (and 805 in FIG. 8) are not electrodes and are non-adhesive regions. Although six electrodes 402 and six blank spaces 404 are shown, other embodiments may include different numbers of electrodes 402, blank spaces 404, or both in the array.

The blank spaces 404 are present at one or more locations that correspond to, or may encompass, relative locations of one or more electrodes 402 upon rotation of the array about the centroid 440 by a first rotation amount (e.g., shown by arrow 438 in FIG. 4B). Upon rotation of the transducer apparatus 400 by a particular rotation amount (e.g., 30, 90, 150, 210, 270, or 330 degrees), the electrodes 402 are located (i.e., new positions shown in FIG. 4B) in areas that were previously (e.g., in FIG. 4A) occupied by the blank spaces 404 between adjacent electrodes 402. In addition, in the position of FIG. 4B, the blank spaces (of former positions shown in FIG. 4A) between electrodes 402 are moved into locations 436 (i.e., 436A-F) that were previously occupied by the electrodes 402. This allows the skin that was previously in contact with or near the electrodes 402 to recover from exposure to the electrodes and/or receive a topical medication, thereby minimizing, reducing, preventing, soothing, healing, and/or treating skin irritation.

As shown in FIGS. 4A and 4B, each electrode 402 of the array may extend in a substantially radial direction (e.g., extending radially outward) away from the centroid 440 of the array. In addition, a centroid of each electrode 402 may be spaced substantially equidistant from the centroid 440 of the array. Each electrode 402 may have a substantially similar shape, and the blank space 404 between two electrodes 402 may have a size sufficient enough to occupy an electrode 402 therein. The electrodes 402 may be spaced substantially equidistant from each other about the centroid 440 of the array. Each electrode 402 may include (as shown with respect to electrode 402A) a first edge 408 extending in a radially outward direction relative to a center portion of the array and a second edge 410 extending in a radially outward direction relative to the center portion of the array. The electrode (e.g., 402A) may further include a rounded edge 412 connecting the first edge 408 to the second edge 410 at an end of the electrode 402A located radially away from the center portion. An outer perimeter 406 substantially tracing the array of electrodes 402 may have a circular shape, although other shapes may be possible.

A relative size of one blank space 404 with respect to an adjacent electrode 402 may be described as follows. A first distance 414 (FIG. 4A) is defined as a distance between a first point 416 on a first outer edge of an electrode (e.g., 402E) and a second point 418 on a second outer edge of the electrode (e.g., 402E), with the first and second points 416/418 each being the same distance 420 from the centroid 440 of the array. A second distance 422 is defined as a distance between the first point 416 and a third point 424 on an adjacent outer edge of a second electrode (e.g., 402D), the adjacent outer edge of the second electrode and the first outer edge being located adjacent each other without any electrodes between them. The first and third points 416/424 are also each the same distance 420 from the centroid 440. The second distance 422 may be at least 80% of the length of the first distance 414. In some embodiments, the second distance 422 may be greater than or equal to the first distance 414. That way, the transducer 400 may provide sufficient space surrounding a portion of the subject's skin that has been previously exposed to an electrode element.

As shown with reference to electrodes 402A and 402F (FIG. 4A), when a bisector 430 is drawn between an outer edge 408 of the electrode 402A and the adjacent outer edge of the electrode 402F, a distance 432 from the outer edge 408 of the electrode 402A to the bisector 430 measured in a direction perpendicular to the bisector 430 equals a distance 434 from the adjacent outer edge to the bisector 430 measured in the direction perpendicular to the bisector 430, along the length of the two outer edges. That is, the outer edges of two adjacent electrodes 402 may have a constant rate of change with respect to their bisector.

A relative shape of one blank space 404 (e.g., 404C, FIG. 4A) with respect to an adjacent electrode 402 (e.g., 402C) may be described as follows. A first angle 426 greater than 0° is formed between a first edge and a second edge of the electrode element (e.g., 402C), the first angle 426 facing exterior to the array. A second angle 428 is formed between the first edge of the electrode element (e.g., 402C) and an adjacent edge of an adjacent electrode element (e.g., 402D), the second angle 428 facing exterior to the array. The value of the second angle 428 may be at least 80% of the value of the first angle 426. In some embodiments, the second angle 428 may be greater than or equal to the first angle 426. That way, the transducer 400 may provide sufficient space surrounding a portion of the subject's skin that has been previously exposed to an electrode element.

Figure 5:
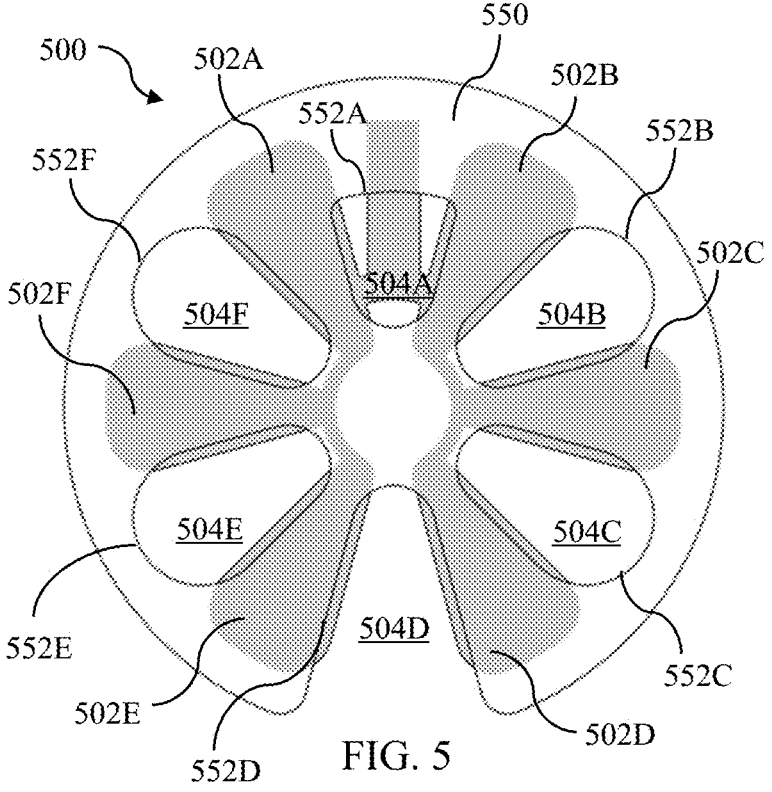
FIG. 5 depicts an example of an adhesive layer connected to an electrode array.
Figure 6:
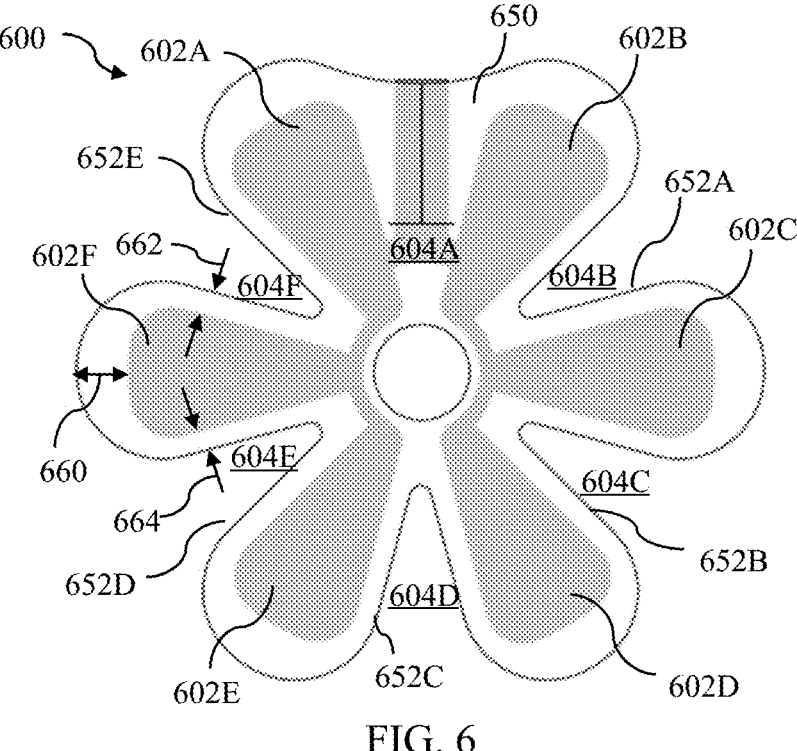
FIG. 6 depicts another example of an adhesive layer connected to an electrode array.

FIGS. 5 and 6 depict example transducer apparatuses 500 and 600, respectively, that may include a similarly shaped array of electrodes 502A-F (i.e., 502) and 602A-F (i.e., 602) as the array of FIG. 4A. In FIGS. 5 and 6, the transducer apparatus (500, 600) includes a substrate in the form of an adhesive layer, or tape bandage with an adhesive layer (550, 650), and an array of electrodes (502, 602) on the substrate. In each of FIGS. 5 and 6, the transducer apparatus (500, 600) includes the array of electrodes (502, 602) with spaces (504A-F, 604A-F) located therebetween. The adhesive layer (550, 650) may be connected to and substantially covering (from beneath) the array of electrodes (502, 602). To further enable the skin on the subject's body to breathe while it is uncovered by an electrode element, the adhesive layer (550, 650) may include one or more cutouts (552A-F, 652A-E) formed therein to leave one or more spaces between the electrodes of the array uncovered. As discussed above, the cut-outs may be cut-outs through both the tape bandage support and the adhesive layer, or just through the adhesive layer (for example, leaving a non-adhesive void region).

In FIG. 5, one or more cutouts 552 may have a closed shape so that the one or more cutouts 552 are surrounded by the adhesive layer 550. The adhesive layer 550 may extend toward but not cover outer edges of one or more electrodes 502 (from the underside), as shown. In FIGS. 5 and 6, one or more cutouts (552, 652) may have an open shape so that the one or more cutouts (552, 652) define one or more concave portions along an outer edge of the adhesive layer (550, 650). The adhesive layer 650 may entirely cover the outer edges of one or more electrodes 602 (from the underside), as shown in FIG. 6. As illustrated with respect to the electrode 602F, the adhesive layer 650 may extend beyond each of the first outer edge (distance 662) and the second outer edge (distance 664) of the electrode 602F by the same amount or by a different amount, and may extend beyond an end edge (distance 660) of the electrode 602F located radially away from the centroid by the same amount (as distance 662 and/or distance 664) or by a different amount. In some embodiments, the adhesive layer may extend beyond an end edge of the electrode located radially away from the centroid (distance 660) by a larger amount (than distance 662 and distance 664). This may enable the adhesive layer 650 to connect the transducer apparatus 600 to a subject's skin without covering too much of the space 604 between adjacent electrodes 602.

Other arrangements of the array of electrodes may enable rotational shifting to minimize, reduce, prevent, soothe, heal, and/or treat skin irritation during TTFields treatment. Various examples of such electrode arrays are shown in FIGS. 7A-7I. The present disclosure is not limited to the arrangements of electrode elements and relief regions (e.g., void regions or medication regions) depicted in these examples, as many others may be possible without departing from the scope of the claims.

Each of FIGS. 7A-7I illustrates an array (700A, 700B, 700C, 700D, 700E, 700F, 700G, 700H, 700I) of electrodes comprising multiple electrode elements (702A, 702B, 702C, 702D, 702E, 702F, 702G, 702H, 702I) and one or more blank spaces where no electrode elements are present. Each blank space may be or may include one or more relief regions (704A, 704B, 704C, 704D, 704E, 704F, 704G, 704H, 704I).

The term "relief regions" 704 (and 804 of FIG. 8) as used herein refers to either 1) void regions of the transducer apparatus that are fully uncovered other than the transducer substrate, 2) non-adhesive regions comprising a medication substrate capable of receiving, absorbing, or holding a topical medication applied thereto, or 3) medication regions of the transducer apparatus comprising a medication substrate and a topical medication integrated therein or thereon used to administer a topical medication to an area of the subject's skin. These relief regions 704 may have no exposed adhesive present.

The electrode elements 702 are positioned in existing electrode positions (708A, 708B, 708C, 708D, 708E, 708F, 708G, 708H, 708I) arranged around a centroid (706A, 706B, 706C, 706D, 706E, 706F, 706G, 706H, 706I) of the array 700. Each of the electrode elements 702 may trace an existing electrode footprint, illustrated via solid outlines in FIGS. 7A-7I. The existing electrode footprints are areal footprints of the existing electrode positions 708. The one or more blank spaces may define potential electrode positions (710A, 710B, 710C, 710D, 710E, 710F, 710G, 710H, 710I), which are positions that might otherwise be occupied by electrode elements 702 upon certain rotations of the array 700. The potential electrode positions 710 are arranged around the centroid 706 of the array, and each potential electrode position 710 traces a potential electrode footprint, illustrated via dashed outlines in FIGS. 7A-7I. The potential electrode footprints are areal footprints of the potential electrode positions 710.

In some embodiments, the relief regions 704 of the array 700 occupy at least the potential electrode positions 710. In an example, the relief regions 704 occupy only the areal footprints defined by the potential electrode positions 710. In another example, the one or more relief regions 704 of an array 700 may occupy greater portion(s) of the blank space(s) between adjacent electrodes 702 than what is defined by the potential electrode positions 710.

In each of FIGS. 7A-7I, at least one relief region 704 in the array 700 is capable of enclosing an areal footprint equivalent to at least 40%, or at least 50%, of the areal footprint of at least one electrode 702, and superimposable on at least 40%, or at least 50%, of the existing electrode position 708 by rotation of the array 700 around the centroid 706. For example, in FIG. 7D, one such relief region 704D(2) is capable of enclosing and superimposable via rotation upon at least 40% of the areal footprint (708D(1)) of the larger electrode element 702D(1). In some embodiments, the at least one relief region 704 in the array is capable of enclosing an areal footprint equivalent to at least 95% (e.g., 100%) of an areal footprint of at least one existing electrode position 708, and superimposable on at least 95% (e.g., 100%) of the existing electrode position 708 by rotation of the array around the centroid 706. For example, in FIG. 7D, a relief region 704D(2) is capable of enclosing and superimposable via rotation upon the entire areal footprint (708D(2)) of the smaller electrode element 702D(2).

In FIGS. 7A-7E, 7H, and 7I, at least one electrode element 702 extends radially outward away from the centroid 706. In FIGS. 7A, 7E, 7H, and 7I, a sum total of the areal footprints for every relief region 704 in the array is approximately 50% of a sum total of the combined areal footprints for every relief region 704 and every existing electrode position 708 of the array. That is, the relief regions 704 take up approximately the same total area as the electrode elements 702 in the transducer apparatus. As shown in each of FIGS. 7A-7I, the sum total of the areal footprints for every relief region 704 in the array may be equivalent to at least 20% of a sum total of the combined areal footprints for every relief region 704 and every existing electrode position 708 of the array, such that the relief regions 704 take up at least one fourth the amount of area as the electrode elements 702 in total.

In some embodiments, each potential electrode footprint (710) has an identical shape, area, orientation with respect to the centroid 706, and distance from the centroid 706, as that of one or more existing electrode footprints (708). In addition, each potential electrode footprint (710) is in rotational coincidence about the centroid 706 with one or more existing electrode footprints (708) such that a rotational shift of the electrode array 700 about the centroid 706 may position at least one potential electrode position 710 to be coincident upon an existing electrode position 708. This rotation provides a resting state (or application of a topical medication) for an area of skin beneath at least one electrode after the rotation. In some embodiments, the total area occupied by potential electrode positions 710 may be no greater than 50% of the sum of the total areas of the potential electrode positions 710 and existing electrode positions 708.

In some embodiments, the combined distribution of potential electrode positions 710 and existing electrode positions 708 in the arrays 700 may exhibit Cx symmetry with respect to rotation about the centroid 706, where x is an integer and the potential electrode footprints are considered to be identical to the existing electrode footprints in determining rotational symmetry of the combined electrode positions 708 and 710. For example, with respect to the combined distribution of potential electrode positions and existing electrode positions, FIG. 7A depicts an array 700A having C12 symmetry, as there are twelve rotationally symmetrical positions about the centroid 706A at which the combined electrode positions 708A/710A may be located; the array 700B of FIG. 7B has C10 symmetry; the array 700C of FIG. 7C has C9 symmetry; The arrays 700D, 700H, and 700I of FIGS. 7D, 7H, and 7I have C2 symmetry; the arrays 700E and 700F of FIGS. 7E and 7F have C8 symmetry; and the array 700G of FIG. 7G has C4 symmetry.

In addition, the rotational symmetry of the existing electrode positions 708 with respect to rotation about the centroid 706 is either Cx', or no rotational symmetry, wherein x' is an integer. For example, FIG. 7A depicts an array 700A having an x' value of six, as there are six rotationally symmetrical existing electrode positions 708. In the examples of FIG. 7A and 7E, the value of x is equivalent to the value of 2x'. In FIG. 7B, the value of x is equivalent to 5x'. In FIG. 7C, the value of x is equivalent to 3x'. In FIG. 7F, the value of x is equivalent to 4x'.

Productive rotations of the array are given by rotations of 360/x degrees and integer multiples thereof except for rotations of 360/x' degrees and integer multiples thereof (which is an unproductive rotation). An "unproductive rotation" results in an equivalent array pattern with the same areas of skin covered by existing electrode positions 708, while a "productive rotation" results in at least one existing electrode position 708 being exchanged for a potential electrode position 710, thus giving the subject's skin space to recover or medication application. In some embodiments, at least one rotation about the centroid 706 results in all potential electrode positions 710 moving to be coincident with positions previously occupied by existing electrode positions 708, thereby providing in a single rotation a resting state (or application of a topical medication) for all areas of skin beneath all of the electrodes in existing electrode positions (for example, arrays 700A, 700E, 700H, 700I).

As shown in FIG. 7D, the existing electrode footprint of at least one electrode element 702D(1) of the array may have a different shape than, and an identical distance from the centroid 706 as, the potential electrode footprint of at least one potential electrode position 710. As shown in FIGS. 7D, 7E, 7G, 7H, and 7I, the existing electrode footprint of at least one electrode element (702D(1), 702E(1), 702G(1), 702H(1), 702I(1)) of the array has a different shape than the existing electrode footprint of at least one other electrode element 702D(2), 702E(2), 702G(2), 702H(2), 702I(2) of the array.

As shown in FIGS. 7E and 7F, the one or more relief regions 704 may define a first potential electrode position (710E(1), 710F(1)) located a first distance from the centroid 706 and a second potential electrode position (710E(2), 710F(2)) located a second distance from the centroid 706, the first and second distances being different from each other. In such instances, the first potential electrode position 710E(1) may be circumferentially offset from the second potential electrode position 710E(2) as in FIG. 7E, or the first potential electrode position 710F(1) may be in radial alignment with the second potential electrode position 710F (2) as in FIG. 7F. In FIG. 7E (and FIGS. 7F and 7G), the array 700E may include a first group of electrode elements 702E arranged in a first circular region 712E around the centroid 706E, and a second group of electrode elements 702E separate from the first group and arranged in a second circular region 714E concentric with the first circular region 712E.

As shown in FIG. 7F, the existing electrode footprint of at least one electrode element 702F(1) of the array 700F may have a different size than the existing electrode footprint of at least one other electrode element 702F(2) of the array 700F. In such instances, the electrode element 702F(1) may have a similar shape as the different sized electrode element 702F(2), as shown (FIG. 7F), or a different shape (FIG. 7G). As shown in FIGS. 7H and 7I, the overall array 700 of electrodes may have a non-circular shape. For example, the array 700 may have an oval, ovaloid, ovoid, or elliptical shape. This allows the array 700 to be used to induce desired TTFields while still providing rotational symmetry for shifting the electrodes with respect to the subject's skin. Both of the arrays 700H and 700I can undergo a 180° rotation about the centroid 706 (706H, 706I) and result in all potential electrode positions 710 moving to be coincident with positions previously occupied by existing electrode positions 708, thereby providing in a single rotation a resting state (or application of a topical medication) for all areas of skin beneath all of the electrodes in existing electrode positions.

FIG. 8 depicts an example transducer apparatus 800 that may be used to apply TTFields to a subject's body. The transducer apparatus 800 may enable a simple translation of the transducer with respect to the subject's body to reposition at least one relief region 804 formed in the electrode array over an area of the subject's skin that was previously covered by an electrode element 802 (an existing electrode position). The relief regions 804A and 804B may be either void regions in the transducer apparatus 800 that are fully uncovered (other than the transducer substrate); or non-adhesive regions comprising a medication substrate capable of receiving, absorbing, or holding a topical medication applied thereto; or medication regions of the transducer apparatus comprising a medication substrate and a topical medication integrated therein or thereon used to administer a topical medication to an area of the subject's skin. In some embodiments, the medication substrate may be a portion of the transducer substrate. Each relief region 804 may be capable of enclosing an areal footprint (potential electrode footprint) equivalent to at least 40%, or at least 50%, or at least 95%, of an areal footprint of at least one of the electrodes 802 of the transducer 800 of FIG. 8. When viewed from the direction perpendicular to the face of the array of electrodes, the electrode elements 802 are positioned in existing electrode positions 808. Each of the electrode elements 802 may trace an existing electrode footprint. The existing electrode footprints are areal footprints of the existing electrode positions 808. The relief regions 804A and 804B may define potential electrode positions 810A and 810B, respectively, which are positions that might otherwise be occupied (i.e., potential electrode footprints) by electrode elements 802 upon certain translations of the transducer array 800. As illustrated, multiple existing electrode positions 808 may be arranged in a line 830. For example, three lines 830A, 830B, and 830C of existing electrode positions 808 are shown in the transducer 800 of FIG. 8. Both relief regions 804A and 804B may be superimposable on at least 40%, or at least 50%, or at least 95%, of the areal footprint of each of the existing electrode positions 808 arranged in an individual line (e.g., 830A, 830B, or 830C) by translation of the array with respect to the subject's body.

Figure 9:
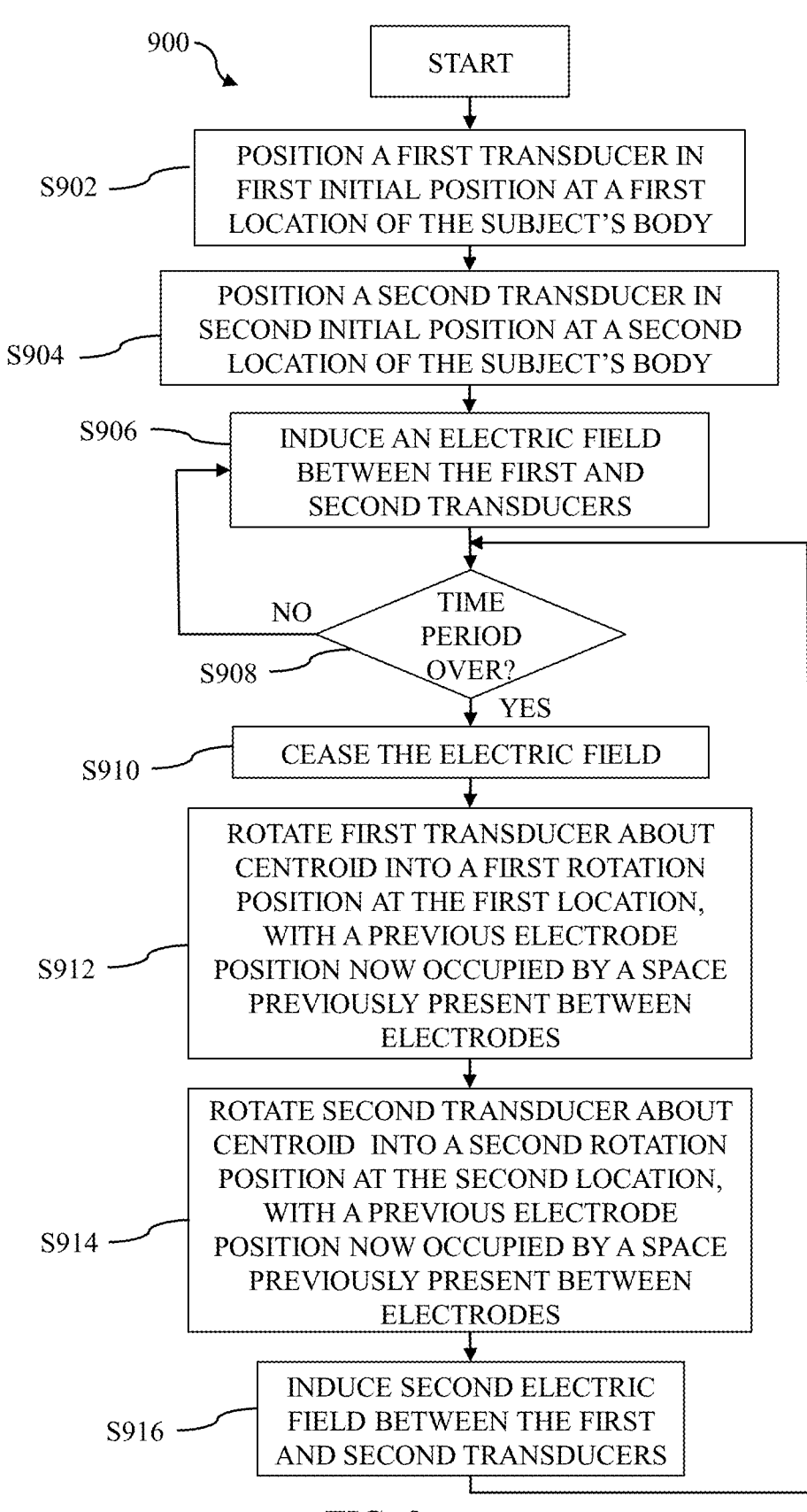
FIG. 9 is a flowchart depicting an example of applying TTFields to a subject's body.

FIG. 9 depicts an example method 900 of applying TTFields to a subject's body in accordance with the present techniques. The method 900 begins at step S902 with positioning a first transducer in a first initial position at a first location of the subject's body. The first transducer may comprise a plurality of electrodes in initial electrode positions arranged circumferentially about a centroid of the first transducer and having a space between at least one pair of adjacent electrodes. The first transducer may be affixed to the subject's body via an adhesive layer that, optionally, has one or more cutouts therein (described above), the cutouts being located over spaces between adjacent electrodes.

At step S904, the method 900 may include positioning a second transducer in a second initial position at a second location of the subject's body. The second transducer may comprise a plurality of electrodes arranged circumferentially about a centroid of the second transducer and having a space between at least one pair of adjacent electrodes. The second transducer may be affixed to the subject's body via an adhesive layer that, optionally, has one or more cutouts therein, the cutouts being located over spaces between adjacent electrodes.

At step S906, the method 900 includes inducing an electric field between the first transducer located at the first location of the subject's body and the second transducer located at the second location of the subject's body. At step S908, the method 900 includes determining whether a first period of time has passed. After inducing the electric field for more than the first period of time, the method 900 proceeds to step S910, which includes ceasing the electric field.

At step S912, the method 900 includes rotating the first transducer about its centroid into a first rotation position at the first location of the subject's body, wherein in the first rotation position at least one of the initial electrode positions is now occupied by a space that was present between two electrodes in the first initial position. In some embodiments, in the first rotation position, all initial electrode positions of the first transducer may now be occupied by spaces that were present between adjacent electrodes in the first initial position.

At step S914, the method 900 may include rotating the second transducer about its centroid into a second rotation position at the second location of the subject's body, wherein in the second rotation position at least one of the initial electrode positions is now occupied by a space that was present between two electrodes in the second initial position. In some embodiments, in the second rotation position, all initial electrode positions of the second transducer may now be occupied by spaces that were present between adjacent electrodes in the second initial position. At step S916, the method 900 includes inducing another electric field between the first transducer and the second transducer.

Figure 10:
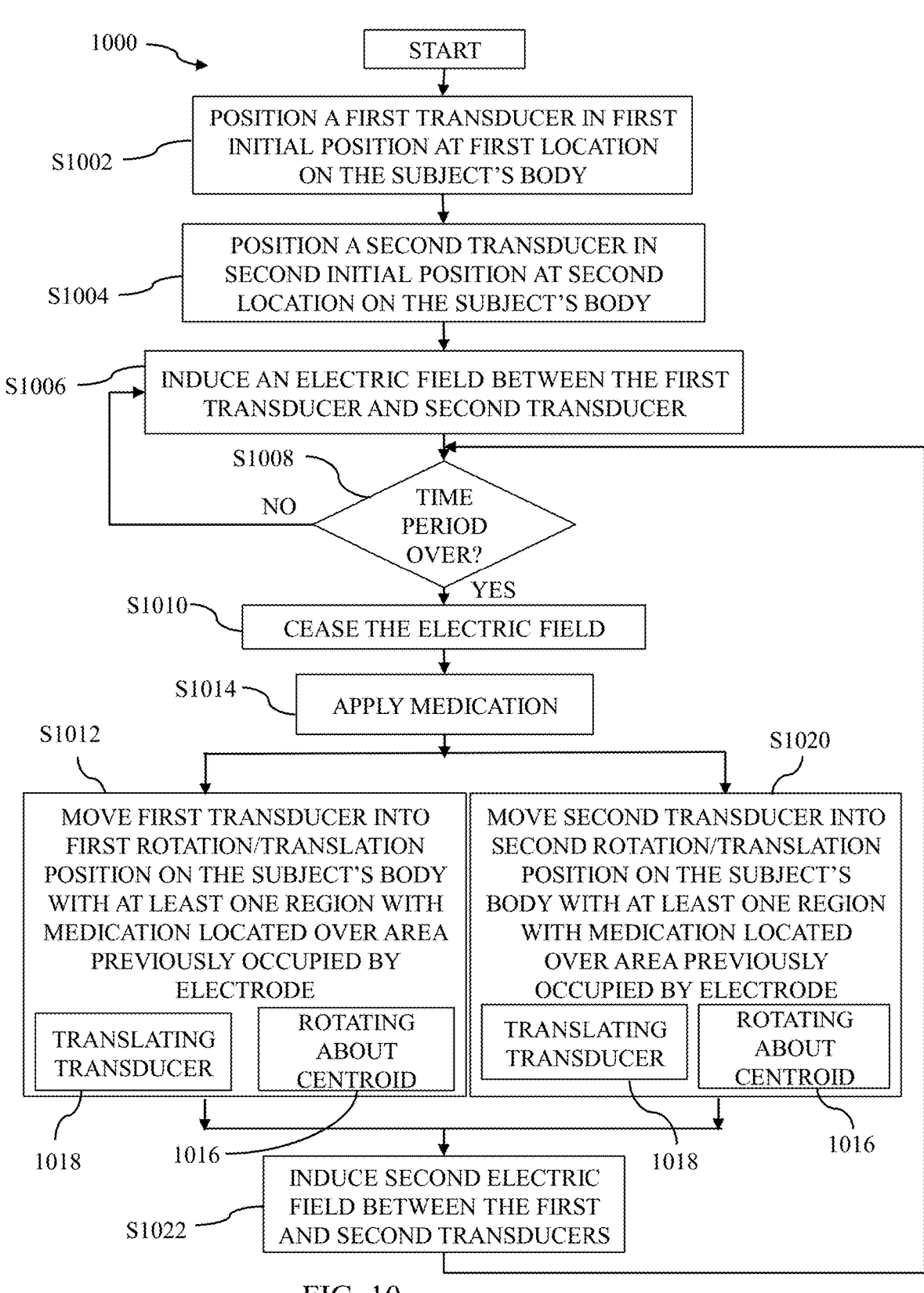
FIG. 10 is a flowchart depicting another example of applying TTFields to a subject's body.

FIG. 10 depicts an example method 1000 of applying TTFields to a subject's body in accordance with the present techniques. The method 1000 begins at step S1002 with positioning a first transducer in a first initial position at a first location of the subject's body. The first transducer may comprise a plurality of electrodes and a medication region located between two adjacent electrodes, the medication region comprising a medication substrate capable of holding a topical medication therein or thereon, and the medication region having no exposed adhesive present thereon. In certain embodiments, the first transducer may include a plurality of medication regions located between adjacent electrodes (e.g., as shown in the apparatuses of FIGS. 4A-8).

At step S1004, the method 1000 may include positioning a second transducer in a second initial position at a second location of the subject's body. The second transducer may comprise a plurality of electrodes in initial electrode positions and a medication region located between two adjacent electrodes, as described above. In certain embodiments, the second transducer may include a plurality of medication regions located between adjacent electrodes (e.g., as shown in the apparatuses of FIGS. 4A-8).

At step S1006, the method 1000 includes inducing an electric field between the first transducer located in a first initial position at the first location of the subject's body and the second transducer in a second initial position located at the second location of the subject's body. At step S1008, the method 1000 includes determining whether a first period of time has passed. After inducing the electric field for more than the first period of time, the method 1000 proceeds to step S1010, which includes ceasing the electric field.

At step S1012, the method 1000 includes moving the first transducer into a first rotation or translation position on the subject's body at the first location, wherein in the first rotation or translation position at least one medication region is holding a topical medication thereon or therein and is in contact with an area of the subject's body that was previously covered by at least a portion of an electrode. In the first rotation or translation position, a plurality of medication regions of the first transducer may each be located in areas that were previously covered by at least a portion of an electrode. In an example, the medication region includes the medication substrate and the topical medication which may be integrated in or on the medication substrate prior to steps S1002 and S1012. In another example, the method 1000 may include, as optional step S1014, applying the topical medication to the medication substrate prior to moving the first transducer into the first rotation or translation position at the first location on the subject's body.

In an example, at step S1012 moving the first transducer to the first rotation or translation position may include rotating (1016) the first transducer about its centroid. In particular, moving the first transducer may include rotating the first transducer about its centroid into a first rotation position at the first location of the subject's body, wherein in the first rotation position at least one medication region is now located over an area that was previously occupied by at least a portion of an electrode in the first initial position. In some embodiments, in the first rotation position, all areas that were previously covered by an electrode in the first initial position may now be occupied by a medication region, and vice-versa. In another example, at step S1012 moving the first transducer to the first rotation or translation position may include translating (1018) the first transducer with respect to a surface of the subject's body to a first translation position.

The method 1000 may also include, at step S1020, moving the second transducer from a second initial position at a second location on the subject's body into a second rotation or translation position on the subject's body (in analogous fashion to that described above for the first transducer in step S1012), wherein in the second rotation or translation position at least one medication region is holding a topical medication thereon or therein and is in contact with an area of the subject's body that was previously covered by at least a portion of an electrode. In the second rotation or translation position, a plurality of medication regions of the second transducer may each be located in areas that were previously covered by at least a portion of an electrode. In an example, the medication region includes the medication substrate and the topical medication which may be integrated in or on the medication substrate prior to steps S1002 and S1020. In another example, the method 1000 may include, as optional step S1014, applying the topical medication to the medication substrate prior to moving the second transducer into the second rotation or translation position at the second location on the subject's body. In an example, at step S1020 moving the second transducer to the second rotation or translation position may include rotating (1016) the second transducer about its centroid (as described above for movement of the first transducer). In another example, at step S1020 moving the second transducer to the second rotation or translation position may include translating (1018) the second transducer with respect to a surface of the subject's body to a second translation position (as described above for movement of the first transducer).

At step S1022, the method 1000 includes inducing another electric field between the first transducer and the second transducer.

The invention includes other illustrative embodiments ("Embodiments") as follows.

Embodiment 1: A transducer apparatus for delivering tumor treating fields to a subject's body, the transducer apparatus comprising: an array of electrodes, the array configured to be positioned over the subject's body with a face of the array facing the subject's body, the array comprising electrode elements positioned in existing electrode positions arranged around a centroid of the array; and at least one void space in the array capable of enclosing an areal footprint equivalent to at least 40%, for example, at least 45%, or at least 50% of an areal footprint of at least one existing electrode position, and superimposable on at least 40%, for example, at least 45%, or at least 50% of at least one existing electrode position by rotation of the array around the centroid.

Embodiment 2: The transducer apparatus of Embodiment 1, wherein the at least one void space in the array is capable of enclosing an areal footprint equivalent to at least 95% of an areal footprint of at least one existing electrode position, and superimposable on at least 95% of at least one existing electrode position by rotation of the array around the centroid.

Embodiment 3: The transducer apparatus of Embodiment 1, wherein a sum total of the areal footprints for every void space in the array is approximately 50% of a sum total of the areal footprints for every void space and every existing electrode position of the array.

Embodiment 4: The transducer apparatus of Embodiment 1, wherein a sum total of the areal footprints for every void space in the array is equivalent to at least 20% of a sum total of the areal footprints for every void space and every existing electrode position of the array.

Embodiment 5: The transducer apparatus of Embodiment 1, wherein the array comprises: a first group of electrode elements positioned in existing electrode positions arranged in a first circular region around the centroid; and a second group of electrode elements different from the first group and positioned in existing electrode positions arranged in a second circular region concentric with the first circular region.

Embodiment 6: A transducer apparatus for delivering tumor treating fields to a subject's body, the transducer apparatus comprising: an array of electrodes, the array configured to be positioned over the subject's body with a face of the array facing the subject's body, said array comprising electrode elements positioned in existing electrode positions arranged around a centroid of the array, and each tracing an existing electrode footprint; the array also comprising one or more void spaces defining potential electrode positions, said potential electrode positions being arranged around the centroid of the array, each potential electrode position tracing a potential electrode footprint, wherein each potential electrode footprint has an identical shape, area, and distance from the centroid, as that of one or more existing electrode footprints, and in rotational coincidence about the centroid with said one or more existing electrode footprints, such that a rotational shift of the electrode array about the centroid may position at least one potential electrode position to be coincident upon an existing electrode position, thereby providing a resting state for an area of skin beneath at least one electrode after the rotation.

Embodiment 6A: The transducer apparatus of Embodiment 6, wherein the total area occupied by potential electrode positions is no greater than 50% of the sum of the total areas of the potential electrode positions and existing electrode positions.

Embodiment 7: The transducer apparatus of Embodiment 6, wherein the array comprises one or more potential electrode positions in one or more void spaces such that the combined distribution of potential electrode positions and existing electrode positions exhibit Cx symmetry with respect to rotation about the centroid, where x is an integer, and wherein the potential electrode footprints are considered to be identical to the existing electrode footprints in determining the rotational symmetry of the combined potential electrode positions and existing electrode positions.

Embodiment 8: The transducer apparatus of Embodiment 6, wherein: the rotational symmetry of the existing electrode positions with respect to rotation about the centroid is either Cx', or no rotational symmetry; the rotational symmetry of the combined distribution of potential electrode positions and existing electrode positions with respect to rotation about the centroid is Cx symmetry; an unproductive rotation results in the same array pattern and the same areas of skin covered for the existing electrode positions, and a productive rotation results in at least one existing electrode position being exchanged for a potential electrode position; wherein x and x' are integers; and wherein the productive rotations are given by rotations of 360/x and integer multiples thereof except for rotations of 360/x' and integer multiples thereof Embodiment 9: The transducer apparatus of Embodiment 8, wherein x is equivalent to 2x', 3x', 4x', or 5x'.

Embodiment 10: The transducer apparatus of Embodiment 6, wherein the existing electrode footprint of at least one electrode element of the array has a different shape than, and an identical distance from the centroid as, the potential electrode footprint of at least one potential electrode position.

Embodiment 11: The transducer apparatus of Embodiment 6, wherein the one or more void spaces define a first potential electrode position located a first distance from the centroid and a second potential electrode position located a second distance from the centroid, the first and second distances being different from each other.

Embodiment 12: The transducer apparatus of Embodiment 6, wherein the existing electrode footprint of at least one electrode element of the array has a different shape or a different size than the existing electrode footprint of at least one other electrode element of the array.

Embodiment 13: The transducer apparatus of Embodiment 6, wherein at least one single rotation about the centroid results in all potential electrode positions moving to be coincident with positions previously occupied by existing electrode positions, thereby providing a resting state for all areas of skin beneath all of the electrodes in existing electrode positions.

Embodiment 14: The transducer apparatus of Embodiment 6, wherein the array of electrodes has a non-circular shape.

Embodiment 15: The transducer apparatus of Embodiment 6, wherein each electrode element extends radially outward away from the centroid.

Embodiment 16: A method of applying tumor treating fields to a subject's body, the method comprising: positioning a first transducer in a first initial position at a first location of the subject's body, the first transducer comprising a plurality of electrodes in initial electrode positions arranged circumferentially about a centroid of the first transducer and having a space between at least one pair of adjacent electrodes; inducing an electric field between the first transducer and a second transducer located at a second location of the subject's body; after inducing the electric field for more than a first period, ceasing the electric field; rotating the first transducer about the centroid into a first rotation position at the first location of the subject's body, wherein in the first rotation position at least one of the initial electrode positions is now occupied by a space that was initially present between two electrodes in the first initial position; and inducing another electric field between the first transducer and the second transducer.

Embodiment 17: The method of Embodiment 16, wherein in the first rotation position all of the initial electrodes positions of the first transducer are now occupied by the spaces initially present between adjacent electrodes in the first initial position.

Embodiment 18: The method of Embodiment 16, further comprising: positioning the second transducer in a second initial position at the second location of the subject's body, the second transducer comprising a plurality of electrodes in initial electrode positions arranged circumferentially about a centroid of the second transducer and having a space between at least one pair of adjacent electrodes; and after inducing the electric field for more than a first period, rotating the second transducer about its centroid into a second rotation position at the second location of the subject's body, wherein in the second rotation position at least one of the second transducer initial electrode positions is now occupied by a space that was initially present between two electrodes in the second initial position; and inducing another electric field between the first transducer and the second transducer.

Embodiment 19: The method of Embodiment 18, wherein in the second rotation position at the second location all of the initial electrode positions of the second transducer are now occupied by the spaces initially present between adjacent electrodes in the second initial position.

Embodiment 20: The method of Embodiment 16, further comprising affixing the first transducer to the subject's body via an adhesive layer, wherein the adhesive layer has one or more cutouts therein, the one or more cutouts being located over the spaces between adjacent electrodes.

Embodiment 21: A transducer apparatus for delivering tumor treating fields to a subject's body, the transducer apparatus comprising: an array of electrodes, the array configured to be positioned over the subject's body with a face of the array facing the subject's body; wherein one or more blank spaces of the transducer apparatus, which do not overlap with any electrodes, are present at one or more locations corresponding to relative locations of one or more electrodes of the array of electrodes upon rotation of the array about a centroid of the array by a first rotation amount.

Embodiment 22: A transducer apparatus for delivering tumor treating fields to a subject's body, the transducer apparatus comprising: an array of electrodes, the array configured to be positioned over the subject's body with a face of the array facing the subject's body; wherein, when viewed from a direction perpendicular to the face of the array, each electrode of the array extends in a substantially radial direction away from a centroid of the array, a centroid of each electrode is spaced substantially equidistant from the centroid of the array; each electrode of the array has a substantially similar shape; and a gap between two electrodes of the array has a size sufficient enough to occupy an electrode therein.

Embodiment 23: A transducer apparatus for delivering tumor treating fields to a subject's body, the transducer apparatus comprising: an array of electrodes, the array configured to be positioned over the subject's body with a face of the array facing the subject's body; wherein, when viewed from a direction perpendicular to the face of the array, each electrode of the array extends in a substantially radial direction away from a centroid of the array, wherein the electrodes are spaced substantially equidistant from each other about the centroid of the array; a first distance is defined as a distance between a first point on a first outer edge of a first electrode and a second point on a second outer edge of the first electrode, the first and second points each being the same distance from the centroid of the array; a second distance is defined as a distance between the first point and a third point on an adjacent outer edge of a second electrode, the adjacent outer edge of the second electrode and the first outer edge being located adjacent each other without any electrodes between them, the first and third points each being the same distance from the centroid of the array; and the second distance is at least 80% of the length of the first distance.

Embodiment 24: The transducer apparatus of Embodiment 23, further comprising an adhesive layer connected to and substantially covering a substrate layer of the array of electrodes, wherein the adhesive layer comprises one or more cutouts formed therein to leave one or more spaces between the electrodes of the array uncovered.

Embodiment 25: The transducer apparatus of Embodiment 24, wherein the one or more cutouts have a closed shape so that the one or more cutouts are surrounded by the adhesive layer when viewed from the direction perpendicular to the face of the array.

Embodiment 26: The transducer apparatus of Embodiment 24, wherein the one or more cutouts have an open shape so that the one or more cutouts define one or more concave portions along an outer edge of the adhesive layer when viewed from the direction perpendicular to the face of the array.

Embodiment 27: The transducer apparatus of Embodiment 23, wherein at least one single rotation about the centroid results in at least one electrode moving to be coincident with a position previously occupied by a space between electrode positions, and at least one position previously occupied by a space between electrode positions moves to be coincident with an electrode.

Embodiment 28: A transducer apparatus for delivering tumor treating fields to a subject's body, the transducer apparatus comprising: an array of electrode elements, the array configured to be positioned over the subject's body with a face of the array facing the subject's body; wherein, when viewed from a direction perpendicular to the face of the array, a first electrode element comprises: a first edge extending in a radially outward direction relative to a center portion of the array; and a second edge extending in a radially outward direction relative to the center portion of the array, wherein a first angle greater than 0° is formed between the first edge and the second edge, the first angle facing exterior to the array; a second electrode element comprises: an adjacent edge extending in a radially outward direction relative to the center portion of the array, the adjacent edge and the first edge being located adjacent each other without any electrode elements between them, wherein a second angle is formed between the first edge and the adjacent edge, the second angle facing exterior to the array; and the value of the second angle is at least 80% of the value of the first angle.

Embodiment 29: The transducer apparatus of Embodiment 8, wherein the electrode elements of the array are spaced substantially equidistant from each other about the array.

Embodiment 30: The transducer apparatus of Embodiment 8, wherein the first electrode further comprises a rounded edge connecting the first edge to the second edge at the end of the electrode element located radially away from the center portion.

Embodiment 31: A transducer apparatus for delivering tumor treating fields to a subject's body, the transducer apparatus comprising: an array of electrodes, the array configured to be positioned over the subject's body with a face of the array facing the subject's body; and a medication region, where no exposed adhesive is present, located between at least one pair of adjacent electrodes of the array when viewed from a direction perpendicular to the face of the array, wherein the medication region comprises: a medication substrate; and a topical medication integrated in or on the medication substrate.

Embodiment 32: The transducer apparatus of Embodiment 31, wherein the topical medication comprises a base component, wherein the base component comprises oil, water, petrolatum, wax, cellulose, or a combination thereof.

Embodiment 33: The transducer apparatus of Embodiment 31, wherein the topical medication comprises at least one of an antibiotic, a steroid, an antiseptic, an emollient, an anesthetic, a terpene, a plant extract, a silicon-based organic polymer, an antifungal agent, a burn relief agent, a skin repair agent, an astringent, or an antihistamine.

Embodiment 34: The transducer apparatus of Embodiment 31, further comprising a transducer substrate, wherein: the array of electrodes is disposed on a surface of the transducer substrate; the transducer substrate comprises an adhesive layer for attaching the transducer apparatus to the subject's body; and the medication substrate is either a portion of the transducer substrate or is disposed on the surface of the transducer substrate.

Embodiment 35: The transducer apparatus of Embodiment 31, wherein the topical medication is substantially evenly distributed through a thickness of the medication substrate.

Embodiment 36: The transducer apparatus of Embodiment 31, wherein, when viewed from the direction perpendicular to the face of the array, the medication region has a surface area sufficient enough to occupy at least 40%, or at least 45%, or at least 50%, or at least 95%, of a surface area of at least one of the electrodes of the array of electrodes.

Embodiment 37: A transducer apparatus for delivering tumor treating fields to a subject's body, the transducer apparatus comprising: an array of electrodes, the array configured to be positioned over the subject's body with a face of the array facing the subject's body; and a non-adhesive region, where no exposed adhesive is present, located between at least one pair of adjacent electrodes of the array, wherein the non-adhesive region comprises (i) a medication substrate capable of at least one of receiving, absorbing, or holding a topical medication applied thereto, and, optionally, (ii) a topical medication integrated in or on the medication substrate; wherein, when viewed from a direction perpendicular to the face of the array, the non-adhesive region is capable of enclosing an areal footprint equivalent to at least 40%, or at least 45%, or at least 50%, or at least 95%, of an areal footprint of at least one of the electrodes of the array of electrodes.

Embodiment 38: The transducer apparatus of Embodiment 37, wherein the medication substrate comprises a cloth, a gauze, a non-woven material, a foam, or a sponge located between the pair of adjacent electrodes.

Embodiment 39: The transducer apparatus of Embodiment 37, wherein, when viewed from the direction perpendicular to the face of the array, the non-adhesive region is capable of enclosing an areal footprint equivalent to at least 95% of an areal footprint of at least one of the electrodes of the array of electrodes.

Embodiment 40: The transducer apparatus of Embodiment 37, wherein, when viewed from the direction perpendicular to the face of the array: the array comprises electrode elements positioned in existing electrode positions arranged around a centroid of the array; and the non-adhesive region is superimposable on at least 40%, or at least 45%, or at least 50%, or at least 95%, of at least one existing electrode position by rotation of the array around the centroid.

Embodiment 41: The transducer apparatus of Embodiment 37, wherein, when viewed from the direction perpendicular to the face of the array: the array comprises electrode elements positioned in existing electrode positions arranged around a centroid of the array, and each tracing an existing electrode footprint; the non-adhesive region encompassing an areal footprint defining a potential electrode position, said potential electrode position being arranged around the centroid of the array and tracing a potential electrode footprint; wherein the potential electrode footprint has an identical shape, area, and distance from the centroid, as that of one or more existing electrode footprints, and is in rotational coincidence about the centroid with said one or more existing electrode footprints, such that a rotational shift of the array about the centroid may position the potential electrode position to be coincident upon an existing electrode position.

Embodiment 42: The transducer apparatus of Embodiment 41, wherein the existing electrode footprint of at least one electrode element of the array has a different shape or a different size than the existing electrode footprint of at least one other electrode element of the array.

Embodiment 43: The transducer apparatus of Embodiment 41, wherein at least one single rotation about the centroid results in all potential electrode positions moving to be coincident with positions previously occupied by existing electrode positions.

Embodiment 44: The transducer apparatus of Embodiment 41, wherein the array of electrodes has a non-circular shape.

Embodiment 45: The transducer apparatus of Embodiment 41, wherein each electrode element extends radially outward away from the centroid.

Embodiment 46: The transducer apparatus of Embodiment 37, wherein, when viewed from the direction perpendicular to the face of the array: the array comprises electrode elements positioned in existing electrode positions, wherein multiple existing electrode positions are arranged in a line; and the non-adhesive region is superimposable on at least 40%, or at least 45%, or at least 50%, or at least 95%, of the areal footprint of each of the existing electrode positions arranged in the line by translation of the array with respect to the subject's body.

Embodiment 47: The transducer apparatus of Embodiment 41, wherein the apparatus comprises at least one non-adhesive region, each encompassing a potential electrode footprint, and wherein a sum total of the areal footprints for every potential electrode footprint is approximately 50% of a sum total of the areal footprints for every potential electrode footprint and every existing electrode footprint in the array of electrodes.

Embodiment 48: The transducer apparatus of Embodiment 41, wherein the apparatus comprises at least one non-adhesive region, each encompassing a potential electrode footprint, and wherein a sum total of the areal footprints for every potential electrode footprint is at least 20% of a sum total of the areal footprints for every potential electrode footprint and every existing electrode footprint in the array of electrodes.

Embodiment 49: The transducer apparatus of Embodiment 37, wherein the array of electrodes comprises: a first group of electrodes arranged in a first circular region around a centroid of the array; and a second group of electrodes different from the first group and arranged in a second circular region concentric with the first circular region.

Embodiment 50: A method of applying tumor treating fields to a subject's body, the method comprising: positioning a first transducer in a first initial position at a first location on the subject's body, the first transducer comprising: a plurality of electrodes in initial electrode positions; and a medication region located between two adjacent electrodes, the medication region comprising a medication substrate capable of holding a topical medication therein or thereon, and the medication region having no exposed adhesive present thereon; inducing an electric field between the first transducer and a second transducer located at a second location on the subject's body; after inducing the electric field for more than a first period, ceasing the electric field; moving the first transducer into a first rotation or translation position on the subject's body, wherein in the first rotation or translation position the medication region is holding a topical medication thereon or therein and is in contact with an area of the subject's body that was previously covered by at least a portion of an electrode; and inducing another electric field between the first transducer and the second transducer.

Embodiment 51: The method of Embodiment 50, wherein the medication region comprises the medication substrate and the topical medication integrated in or on the medication substrate prior to positioning the first transducer in the first initial position on the subject's body.

Embodiment 52: The method of Embodiment 50, further comprising applying the topical medication to the medication substrate after positioning the first transducer in the first initial position but prior to moving the first transducer into the first rotation or translation position on the subject's body.

Embodiment 53: The method of Embodiment 50, wherein moving the first transducer into the first rotation or translation position comprises rotating the first transducer about a centroid of the first transducer.

Embodiment 54: The method of Embodiment 50, wherein moving the first transducer into the first rotation or translation position comprises translating the first transducer with respect to a surface of the subject's body.

Embodiment 55: The method of Embodiment 50, wherein the first transducer comprises a plurality of medication regions including the medication region, wherein each medication region of the plurality of medication regions is located between adjacent electrodes of the plurality of electrodes, and wherein in the first rotation or translation position each medication region of the plurality of medication regions of the first transducer are located in areas that were previously covered by at least a portion of an electrode.

Embodiment 56: The method of Embodiment 50, further comprising: positioning the second transducer in a second initial position at the second location of the subject's body, the second transducer comprising: a plurality of electrodes; and a medication region located between two adjacent electrodes, the medication region comprising a medication substrate capable of holding a topical medication thereon, and the medication region having no exposed adhesive present thereon; and after inducing the electric field for more than a first period, moving the second transducer into a second rotation or translation position on the subject's body, wherein in the second rotation or translation position the medication region of the second transducer is holding a topical medication thereon or therein and is in contact with an area of the subject's body that was previously covered by at least a portion of an electrode of the second transducer; and inducing another electric field between the first transducer and the second transducer.

Embodiment 57: The method of Embodiment 56, wherein the second transducer comprises a plurality of medication regions including the medication region, wherein each medication region of the plurality of medication regions is located between adjacent electrodes of the plurality of electrodes, and wherein in the second rotation or translation position each medication region of the plurality of medication regions of the second transducer are located in areas that were previously covered by at least a portion of an electrode of the second transducer.

Embodiment 58: A transducer apparatus for delivering tumor treating fields to a subject's body, the transducer apparatus comprising: an array of electrodes, the array configured to be positioned over the subject's body with a face of the array facing the subject's body, said array comprising electrode elements positioned in existing electrode positions arranged around a centroid of the array; and at least one medication region located between a pair of electrodes in the array, the at least one medication region comprising a medication substrate capable of at least one of receiving, absorbing, or holding a topical medication thereon or therein, and the at least one medication region capable of enclosing an areal footprint equivalent to at least 40%, or at least 45%, or at least 50%, or at least 95%, of an areal footprint of at least one existing electrode position, and superimposable on at least 40%, or at least 45%, or at least 50%, or at least 95%, of at least one existing electrode position by rotation of the array around the centroid.

Embodiment 59: A transducer apparatus for delivering tumor treating fields to a subject's body, the transducer apparatus comprising: an array of electrodes, the array configured to be positioned over the subject's body with a face of the array facing the subject's body, said array comprising electrode elements positioned in existing electrode positions arranged around a centroid of the array, and each tracing an existing electrode footprint; the array also comprising one or more medication regions encompassing an areal footprint defining potential electrode positions, said potential electrode positions being arranged around the centroid of the array, each potential electrode position tracing a potential electrode footprint, wherein each medication region comprises (i) a substrate capable of at least one of receiving, absorbing, or holding a topical medication thereon or therein, and, optionally, (ii) a topical medication integrated in or on the medication substrate; wherein each potential electrode footprint has an identical shape, area, and distance from the centroid, as that of one or more existing electrode footprints, and in rotational coincidence about the centroid with said one or more existing electrode footprints, such that a rotational shift of the electrode array about the centroid may position at least one potential electrode position to be coincident upon an existing electrode position, thereby after the rotation providing a resting state or applying the topical medication to an area of skin formerly beneath at least one electrode.

Embodiment 59A: The transducer apparatus of Embodiment 59, wherein the total area occupied by potential electrode positions is no greater than 50% of the sum of the total areas of the potential electrode positions and existing electrode positions.

Embodiment 60: The transducer apparatus of Embodiment 59, wherein at least one single rotation about the centroid results in all potential electrode positions moving to be coincident with positions previously occupied by existing electrode positions, thereby providing either a resting state or applying the topical medication for areas of skin beneath all of the electrodes in existing electrode positions.

Embodiment 61: The transducer apparatus of Embodiment 59, wherein the array of electrodes has a non-circular shape.

Embodiment 62: The transducer apparatus of Embodiment 59, wherein each electrode element extends radially outward away from the centroid.

Embodiment 63: The transducer apparatus of Embodiment 59, wherein the topical medication is a cream, an ointment, a lotion, a gel, a wax, a paste, or a mineral oil jelly.

Embodiments illustrated under any heading or in any portion of the disclosure may be combined with embodiments illustrated under the same or any other heading or other portion of the disclosure unless otherwise indicated herein or otherwise clearly contradicted by context. For example, and without limitation, embodiments described in dependent claim format for a given embodiment (e.g., the given embodiment described in independent claim format) may be combined with other embodiments (described in independent claim format or dependent claim format).

Numerous modifications, alterations, and changes to the described embodiments are possible without departing from the scope of the present invention defined in the claims. It is intended that the present invention not be limited to the described embodiments, but that it has the full scope defined by the language of the following claims, and equivalents thereof

What is claimed is:

1. A transducer apparatus for delivering tumor treating fields to a subject's body, the transducer apparatus comprising:

an array of electrodes, the array configured to be positioned over the subject's body with a face of the array facing the subject's body, the array comprising electrode elements positioned in existing electrode positions arranged around a centroid of the array; and at least one void space in the array capable of enclosing an areal footprint equivalent to at least 40% of an areal footprint of at least one existing electrode position, and superimposable on at least 40% of at least one existing electrode position by rotation of the array around the centroid.

2. The transducer apparatus of claim 1, wherein the at least one void space in the array is capable of enclosing an areal footprint equivalent to at least 95% of an areal footprint of at least one existing electrode position, and superimposable on at least 95% of at least one existing electrode position by rotation of the array around the centroid.

3. The transducer apparatus of claim 1, wherein a sum total of the areal footprints for every void space in the array is approximately 50% of a sum total of the areal footprints for every void space and every existing electrode position of the array.

4. The transducer apparatus of claim 1, wherein a sum total of the areal footprints for every void space in the array is equivalent to at least 20% of a sum total of the areal footprints for every void space and every existing electrode position of the array.

5. The transducer apparatus of claim 1, wherein the array comprises:

a first group of electrode elements positioned in existing electrode positions arranged in a first circular region around the centroid; and a second group of electrode elements different from the first group and positioned in existing electrode positions arranged in a second circular region concentric with the first circular region.

6. A transducer apparatus for delivering tumor treating fields to a subject's body, the transducer apparatus comprising:

an array of electrodes, the array configured to be positioned over the subject's body with a face of the array facing the subject's body, said array comprising electrode elements positioned in existing electrode positions arranged around a centroid of the array, and each tracing an existing electrode footprint;

the array also comprising one or more void spaces defining potential electrode positions, said potential electrode positions being arranged around the centroid of the array, each potential electrode position tracing a potential electrode footprint, wherein each potential electrode footprint has an identical shape, area, and distance from the centroid, as that of one or more existing electrode footprints, and in rotational coincidence about the centroid with said one or more existing electrode footprints, such that a rotational shift of the electrode array about the centroid may position at least one potential electrode position to be coincident upon an existing electrode position, thereby providing a resting state for an area of skin beneath at least one electrode after the rotation.

7. The transducer apparatus of claim 6, wherein the total area occupied by potential electrode positions is no greater than 50% of the sum of the total areas of the potential electrode positions and existing electrode positions.

8. The transducer apparatus of claim 6, wherein the array comprises one or more potential electrode positions in one or more void spaces such that the combined distribution of potential electrode positions and existing electrode positions exhibit Cx symmetry with respect to rotation about the centroid, where x is an integer, and wherein the potential electrode footprints are considered to be identical to the existing electrode footprints in determining the rotational symmetry of the combined potential electrode positions and existing electrode positions.

9. The transducer apparatus of claim 8, wherein the Cx symmetry is C2 symmetry, C4 symmetry, C8 symmetry, C9 symmetry, C10 symmetry, or C12 symmetry.

10. The transducer apparatus of claim 8, wherein the Cx symmetry is C8 symmetry, C10 symmetry, or C12 symmetry.

11. The transducer apparatus of claim 6, wherein:

the rotational symmetry of the existing electrode positions with respect to rotation about the centroid is either Cx', or no rotational symmetry;

the rotational symmetry of the combined distribution of potential electrode positions and existing electrode positions with respect to rotation about the centroid is Cx symmetry;

an unproductive rotation results in the same array pattern and the same areas of skin covered for the existing electrode positions, and a productive rotation results in at least one existing electrode position being exchanged for a potential electrode position;

wherein x and x' are integers; and wherein the productive rotations are given by rotations of 360/x and integer multiples thereof except for rotations of 360/x' and integer multiples thereof;

optionally, wherein x is equivalent to 2x', 3x', 4x', or 5x'.

12. The transducer apparatus of claim 11, wherein there are 6 existing electrode positions, and wherein the rotational symmetry of the existing electrode positions with respect to rotation about the centroid is C6 and the rotational symmetry of the combined distribution of potential electrode positions and existing electrode positions with respect to rotation about the centroid is C12 symmetry.

13. The transducer apparatus of claim 6, wherein the existing electrode footprint of at least one electrode element of the array has a different shape than, and an identical distance from the centroid as, the potential electrode footprint of at least one potential electrode position.

14. The transducer apparatus of claim 6, wherein the one or more void spaces define a first potential electrode position located a first distance from the centroid and a second potential electrode position located a second distance from the centroid, the first and second distances being different from each other.

15. The transducer apparatus of claim 6, wherein the existing electrode footprint of at least one electrode element of the array has a different shape or a different size than the existing electrode footprint of at least one other electrode element of the array.

16. The transducer apparatus of claim 6, wherein at least one single rotation about the centroid results in all potential electrode positions moving to be coincident with positions previously occupied by existing electrode positions, thereby providing a resting state for all areas of skin beneath all of the electrodes in existing electrode positions.

17. The transducer apparatus of claim 16, wherein there are 6 existing electrode positions.

18. The transducer apparatus of claim 6, wherein the array of electrodes has a non-circular shape.

19. The transducer apparatus of claim 6, wherein each electrode element extends radially outward away from the centroid.

20. The transducer apparatus of claim 6, wherein said array comprising electrode elements has 6 electrode elements positioned in existing electrode positions arranged around a centroid of the array, and each tracing an existing electrode footprint.

* * * * *